(12) United States Patent
Ge

(10) Patent No.: US 12,012,415 B2
(45) Date of Patent: Jun. 18, 2024

(54) COMPOSITIONS AND METHODS FOR THE DIAGNOSIS, TREATMENT AND PREVENTION OF NEOPLASTIC AND NEUROLOGICAL DISORDERS

(71) Applicant: AscentGene, Inc., Gaithersburg, MD (US)

(72) Inventor: Hui Ge, Gaithersburg, MD (US)

(73) Assignee: AscentGene, Inc., Gaithersburg, MD (US)

( * ) Notice: Subject to any disclaimer, the term of this patent is extended or adjusted under 35 U.S.C. 154(b) by 795 days.

(21) Appl. No.: 16/973,119

(22) PCT Filed: Jun. 27, 2019

(86) PCT No.: PCT/US2019/039481
§ 371 (c)(1),
(2) Date: Dec. 8, 2020

(87) PCT Pub. No.: WO2020/006215
PCT Pub. Date: Jan. 2, 2020

(65) Prior Publication Data
US 2021/0253590 A1 Aug. 19, 2021

Related U.S. Application Data

(60) Provisional application No. 62/691,267, filed on Jun. 28, 2018.

(51) Int. Cl.
| | | |
|---|---|---|
| *C07D 487/22* | (2006.01) | |
| *A61K 9/00* | (2006.01) | |
| *A61K 9/19* | (2006.01) | |
| *A61K 31/409* | (2006.01) | |
| *A61K 39/39* | (2006.01) | |
| *A61P 25/28* | (2006.01) | |
| *A61P 35/00* | (2006.01) | |

(52) U.S. Cl.
CPC .......... *C07D 487/22* (2013.01); *A61K 9/0019* (2013.01); *A61K 9/19* (2013.01); *A61K 39/39* (2013.01); *A61P 25/28* (2018.01); *A61P 35/00* (2018.01)

(58) Field of Classification Search
CPC ..... C07D 487/22; A61K 31/409; A61P 35/00; A61P 25/28
See application file for complete search history.

(56) References Cited

FOREIGN PATENT DOCUMENTS

| EP | 0335539 A2 | 10/1989 | |
|---|---|---|---|
| WO | WO 2017/197104 A1 * | 11/2017 | ........... A61K 31/409 |
| WO | WO 2020/237203 | 11/2020 | |

OTHER PUBLICATIONS

PubChem CID 132118563 https://pubchem.ncbi.nlm.nih.gov/compound/132118563, record created Jan. 29, 2018, accessed Sep. 27, 2023.*
The Merck Manual http://www.merckmanuals.com/professional accessed Jan. 27, 2024.*
The National Cancer Institute National Cancer Institute at the National Institutes of Health, A to Z List of Cancers, http://www.cancer.gov/cancertopics/types/alphalist#b accessed Jan. 27, 2024.*
Zhang et al. PloS ONE 2020, 15 (3), e0230670, pp. 1-16.*
Neurological disorders, John Hopkins Medicine https://www.hopkinsmedicine.org/health/conditions-and-diseases/neurological-disorders accessed Jan. 27, 2024.*
Search Report for EPO Application No. 19 824 578.9 dated Feb. 15, 2022.
Examination Report for EPO Application No. 19 824 578.9 dated Feb. 15, 2022.
PubChem Online Database Accession No. 329751495 dated Mar. 3, 2017.
Stockl Caroline: NDA 21-119/SCM-004 Medical Review; Drug Approval Package Visudyne (Verteporfin) Injection dated Mar. 4, 2005.
Al-Moujahed et al., "Verteporfin inhibits growth of human glioma in vitro without light activation" Scientific Reports vol. 7(1):1-8 (Aug. 8, 2017.
Examination Report for CN Application No. 201980056369.5 dated Jun. 1, 2023.
Examination Report for CN Application No. 201980056369.5 dated Jun. 1, 2023—translated.
Examination Report for EPO Application No. 19 824 578.9 dated Mar. 20, 2023.
Examination Report for CN Application No. 201980056369.5 dated Feb. 22, 2024.
Examination Report for CN Application No. 201980056369.5 dated Feb. 22, 2024—translated.

* cited by examiner

*Primary Examiner* — Irina Neagu
(74) *Attorney, Agent, or Firm* — Remenick PLLC

(57) ABSTRACT

The invention is directed to composition and methods for the diagnosis, treatment and prevention of various disorders including but not limited to cancer and neurological disorders. In particular, the invention is directed to compositions and methods for the inhibition of PC4.

22 Claims, 31 Drawing Sheets

| DRUG CANDIDATE | AG-1031 | AG-1503 | AG-1601 |
|---|---|---|---|
| TRADE NAME | VERTEPORFIN | COPROPORPHYRIN III TETRAMETHYL ESTER | NEWLY SYNTHESIZED |
| MOL WEIGHT | 718.794 | 710.83 | 679.86 |
| CAS# | 129497-78-5 | 5522-63-4 | (WJUS01-241-1a) |
| INDICATION | NSCLC/GLIOMA | GLIOMA (NSCLC & AD) | (GLIOMA & NSCLC) |
| STATUS | FDA APPROVED | IN MARKET | NEW |

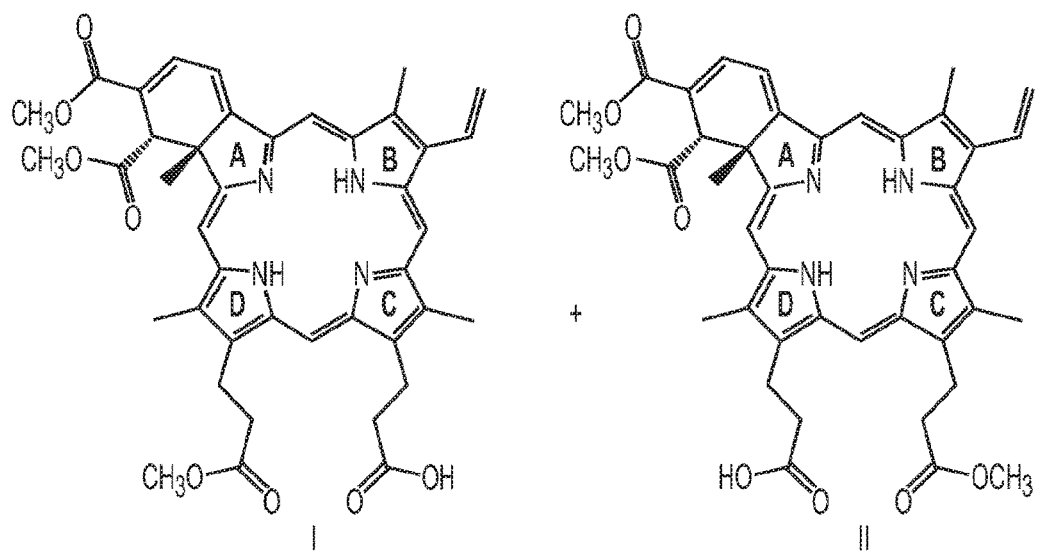
FIG. 3
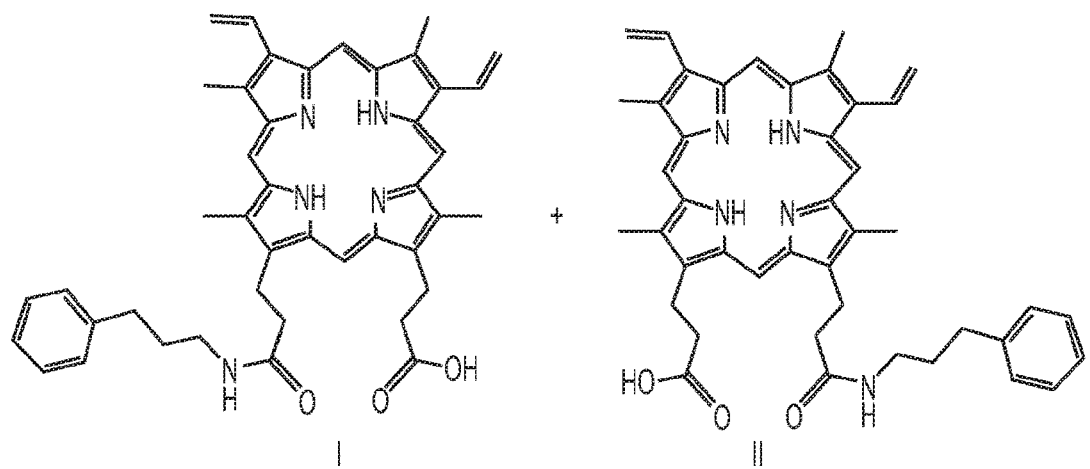
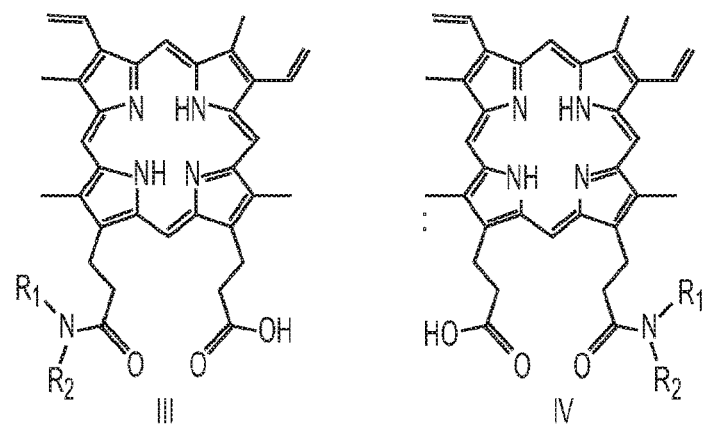
FIG. 4

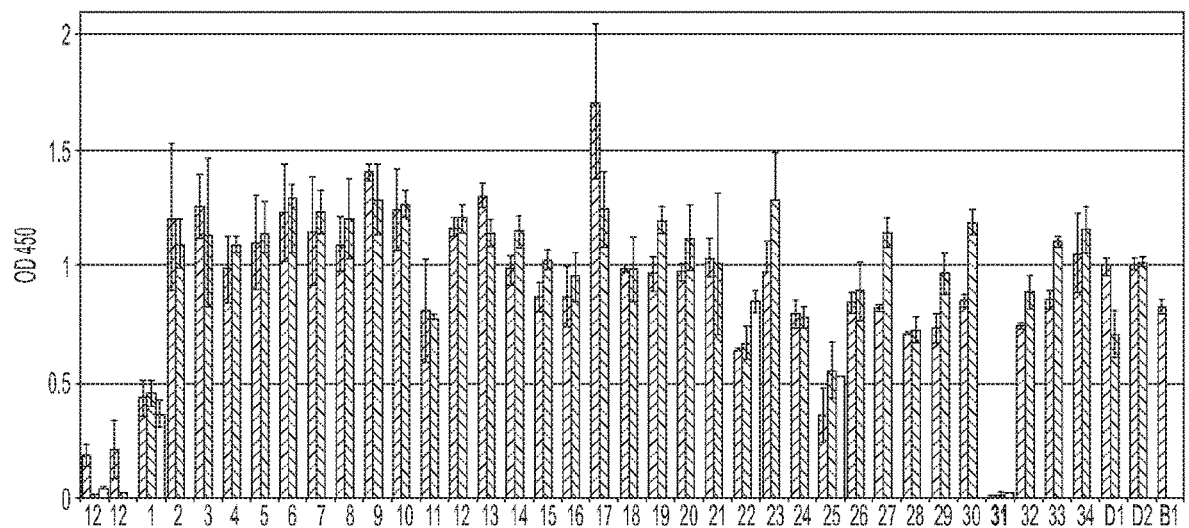
FIG. 5
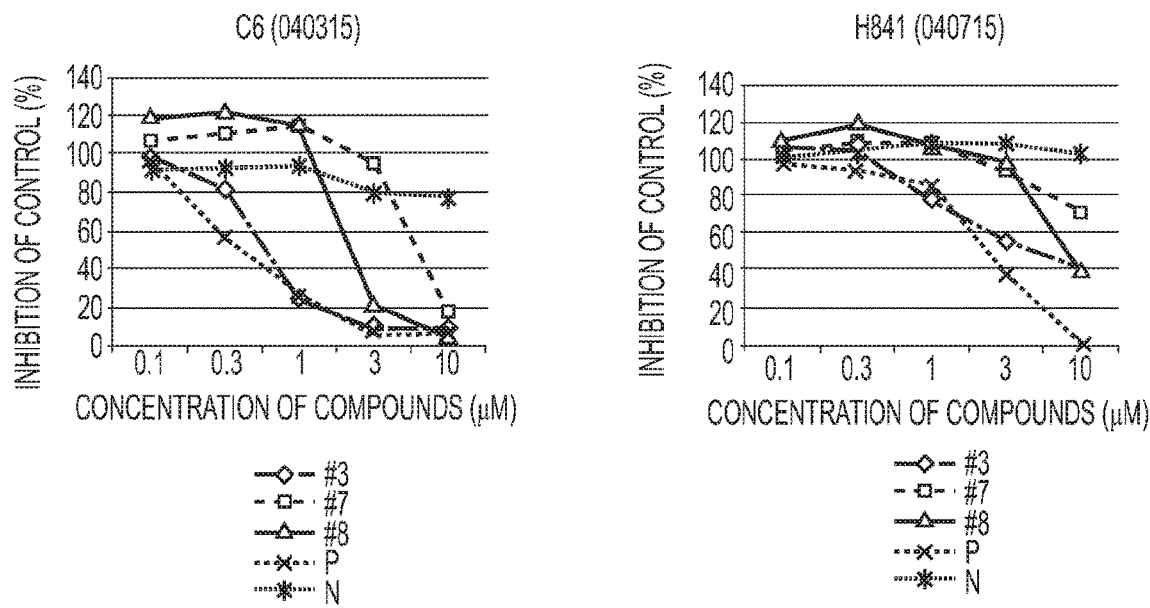
FIG. 6A
FIG. 6B

AG-1031 PREVENTS NSCLC FORMATION

| VACCINE 2 ID (WO899) | | DAY 1 | DAY 5 | DAY 7 | DAY 14 | DAY 21 | DAY 27 | DAY 35 |
|---|---|---|---|---|---|---|---|---|
| | #897 | 0.0 | 0.0 | 4.2 | 2.8 | 18.0 | 56.1 | 113.1 |
| | #898 | 0.0 | 0.0 | 8.2 | 2.8 | 14.1 | 27.6 | 65.4 |
| | #900 | 0.0 | 0.0 | 0.0 | 1.8 | 2.8 | 10.9 | 22.4 |
| | #901 | 0.0 | 0.0 | 0.0 | 0.0 | 0.0 | 0.0 | 0.0 |
| | #902 | 0.0 | 18.0 | 10.9 | 14.1 | 56.1 | 87.1 | 143.8 |
| | Ave. 2 | 0.0 | 3.6 | 4.7 | 4.3 | 18.2 | 36.3 | 69.0 |

| CONTROL | ID | DAY 1 | DAY 5 | DAY 7 | DAY 14 | DAY 21 | DAY 27 | DAY 35 |
|---|---|---|---|---|---|---|---|---|
| | #903 | 0.0 | 27.6 | 33.5 | 40.2 | 75.8 | 179.6 | 381.7 |
| | #904 | 0.0 | 56.1 | 56.1 | 65.4 | 127.8 | 268.1 | 350.8 |
| | #905 | 0.0 | 75.8 | 56.1 | 75.8 | 127.8 | 220.9 | 321.6 |
| | #906 | 0.0 | 33.5 | 40.2 | 56.1 | 75.8 | 127.8 | 220.9 |
| | #907 | 0.0 | 22.4 | 27.6 | 40.2 | 87.1 | 179.6 | 321.6 |
| | #908 | 0.0 | 33.5 | 40.2 | 27.6 | 47.7 | 127.8 | 220.9 |
| | Ave. | 0.0 | 41.5 | 42.3 | 50.9 | 90.3 | 184.0 | 302.9 |

VACCINE GROUP (TOP) CONTROL GROUP (BOTTOM)

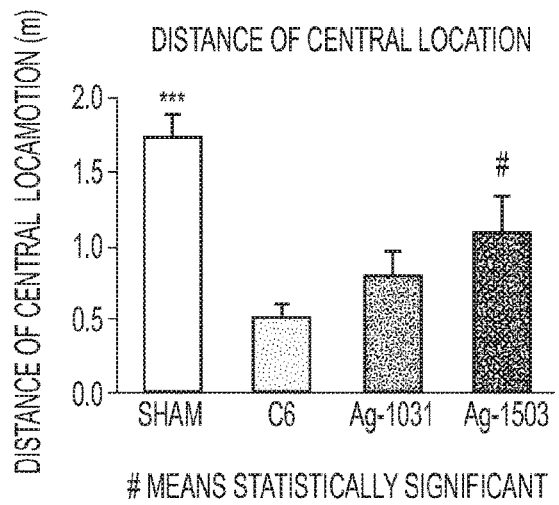
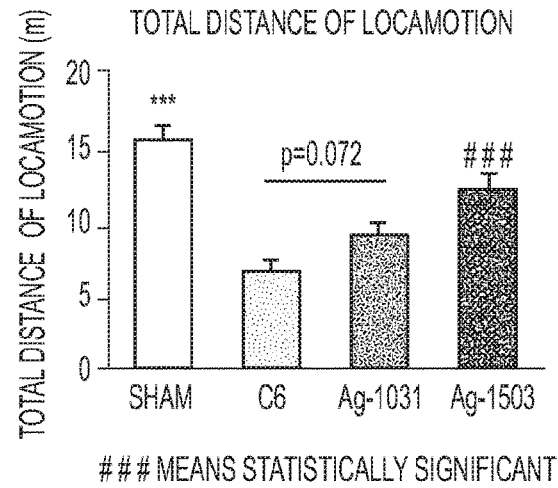
FIG. 14A  FIG. 14B
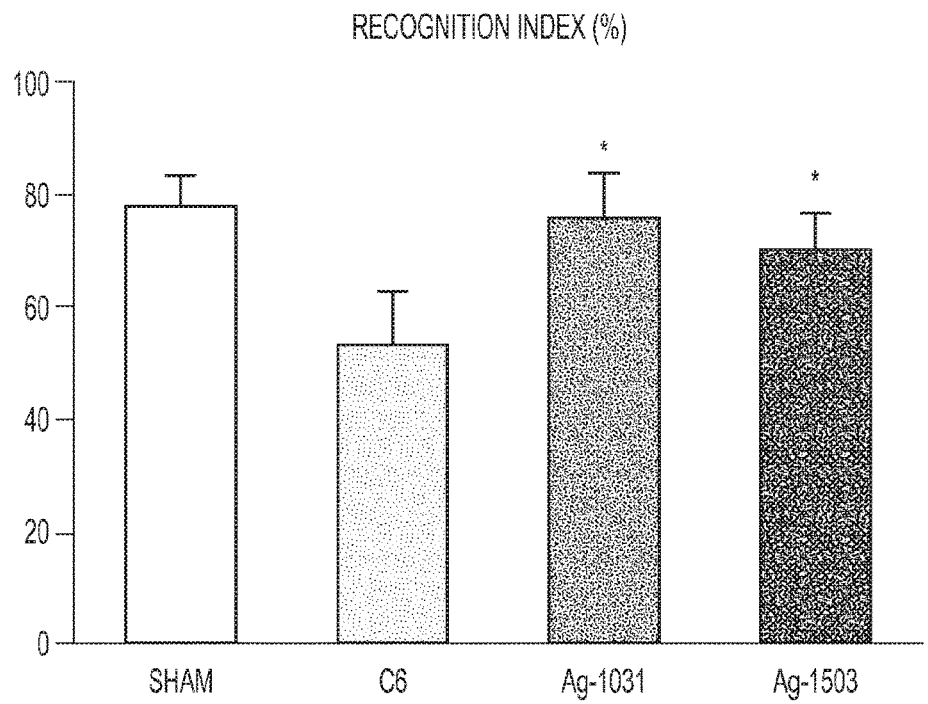
FIG. 15

(#1=AG-1601, #10 = AG-1610)

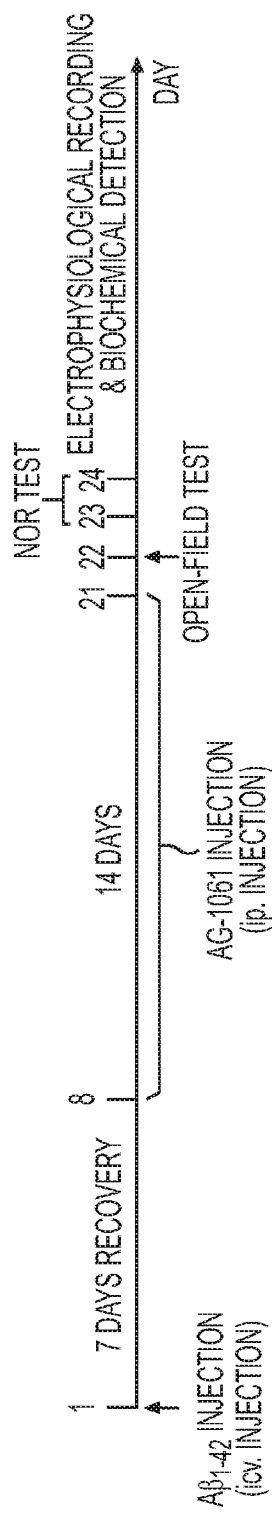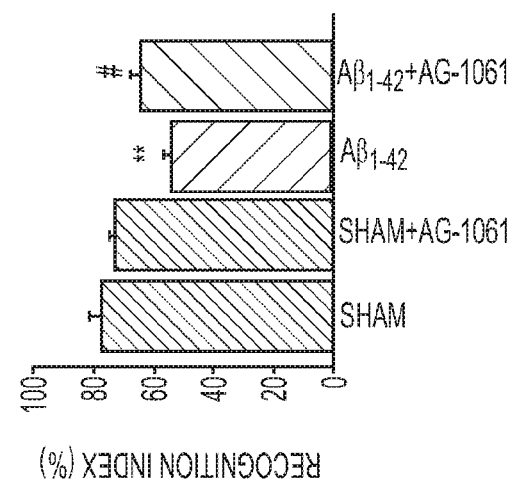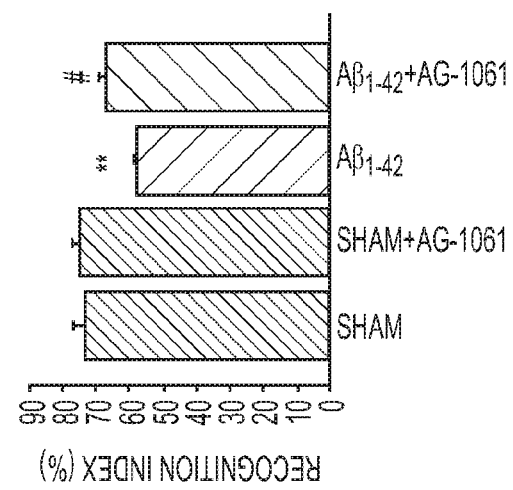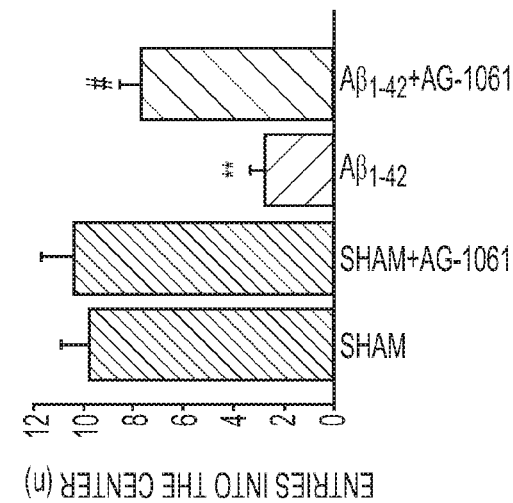
FIG. 20A
FIG. 20B
FIG. 20C
FIG. 20D

EFFICACY OF AG-1601 IN RAT CELLS

| OD450-1H | C6 | U251 | SF-295 | SF-539 |
|---|---|---|---|---|
| VEHICLE | 100 | 100 | 100 | 100 |
| 0.1µM | 106 | 101 | 142 | 112 |
| 0.3µM | 111 | 105 | 136 | 113 |
| 1µM | 109 | 112 | 138 | 119 |
| 3µM | 45 | 75 | 124 | 87 |
| 10µM | 17 | 6 | 35 | 11 |
| 30µM | 10 | 5 | 9 | 10 |
| 100µM | 3 | 2 | 4 | 6 |

EFFICACY OF AG-1601 IN HUMAN GLIOMA CELLS

| OD450-1H | C6 | U251 | SF-295 | SF-539 |
|---|---|---|---|---|
| VEHICLE | 100 | 100 | 100 | 100 |
| 0.1μM | 103 | 103 | 134 | 106 |
| 0.3μM | 106 | 104 | 129 | 107 |
| 1μM | 105 | 106 | 128 | 115 |
| 3μM | 39 | 91 | 115 | 76 |
| 10μM | 5 | 1 | 23 | 1 |
| 30μM | 1 | 1 | 1 | 1 |
| 100μM | 0 | 1 | 2 | 1 |

EFFICACY OF DIFFERENT BATCH OF AG-1601 IN C6 AND U251 GLIOMA CELLS

| AG-1601 | C6 | | U251 | |
|---|---|---|---|---|
| OD450-1H | OLD | NEW | OLD | NEW |
| VEHICLE | 100 | 100 | 100 | 100 |
| 0.1μM | 110 | 123 | 118 | 111 |
| 0.3μM | 110 | 128 | 120 | 117 |
| 1μM | 112 | 126 | 119 | 111 |
| 3μM | 52 | 56 | 82 | 85 |
| 10μM | 9 | 11 | 8 | 10 |
| 30μM | 6 | 8 | 2 | 2 |
| 100μM | 7 | 15 | 2 | 2 |

EFFICACY OF AG-1601 IN C6 AND U87 GLIOMA CELLS

| OD450 | C6 | U87 |
|---|---|---|
| VEHICLE | 100 | 100 |
| 0.1 μM | 104 | 115 |
| 0.3 μM | 104 | 110 |
| 1 μM | 91 | 95 |
| 3 μM | 52 | 57 |
| 10 μM | 3 | 5 |
| 30 μM | 3 | 6 |
| 100 μM | 4 | 12 |

EFFICACY OF AG-1601, TMZ, AND CARMUSTINE IN U251 CELLS

| OD450 | AG-1601 | TMZ | CARMU |
|---|---|---|---|
| DMSO | 100 | 100 | 100 |
| 0.1μM | 105 | 106 | 103 |
| 0.3μM | 110 | 114 | 109 |
| 1μM | 99 | 116 | 112 |
| 3μM | 64 | 112 | 104 |
| 10μM | 9 | 101 | 87 |
| 30μM | 7 | 99 | 67 |
| 100μM | 8 | 86 | 38 |

EFFICACY OF AG-1601, TMZ, AND CARMUSTINE IN U87 CELLS

| OD450 | AG-1601 | TMZ | CARMU |
|---|---|---|---|
| DMSO | 100 | 100 | 100 |
| 0.1μM | 117 | 110 | 99 |
| 0.3μM | 115 | 94 | 86 |
| 1μM | 101 | 108 | 98 |
| 3μM | 36 | 98 | 102 |
| 10μM | 9 | 99 | 106 |
| 30μM | 8 | 91 | 108 |
| 100μM | 10 | 76 | 74 |

AG-1601 POTENTIATES THE EFFECT OF TMZ IN U251 CELLS

| OD450 | AG-1601 | TMZ | AG-1601+TMZ |
|---|---|---|---|
| DMSO | 100 | 100 | 100 |
| 0.1μM | 127 | 131 | 101 |
| 0.3μM | 132 | 127 | 105 |
| 1μM | 115 | 126 | 64 |
| 3μM | 81 | 110 | 18 |
| 10μM | 12 | 112 | 4 |
| 30μM | 7 | 106 | 5 |
| 100μM | 7 | 94 | 7 |

AG-1601 POTENTIATES THE EFFECT OF TMZ IN U87 CELLS

| OD450 | AG-1601 | TMZ | AG-1601+TMZ |
|---|---|---|---|
| DMSO | 100 | 100 | 100 |
| 0.1μM | 156 | 150 | 60 |
| 0.3μM | 143 | 129 | 64 |
| 1μM | 133 | 128 | 62 |
| 3μM | 75 | 122 | 42 |
| 10μM | 9 | 115 | 10 |
| 30μM | 9 | 115 | 7 |
| 100μM | 14 | 98 | 16 |

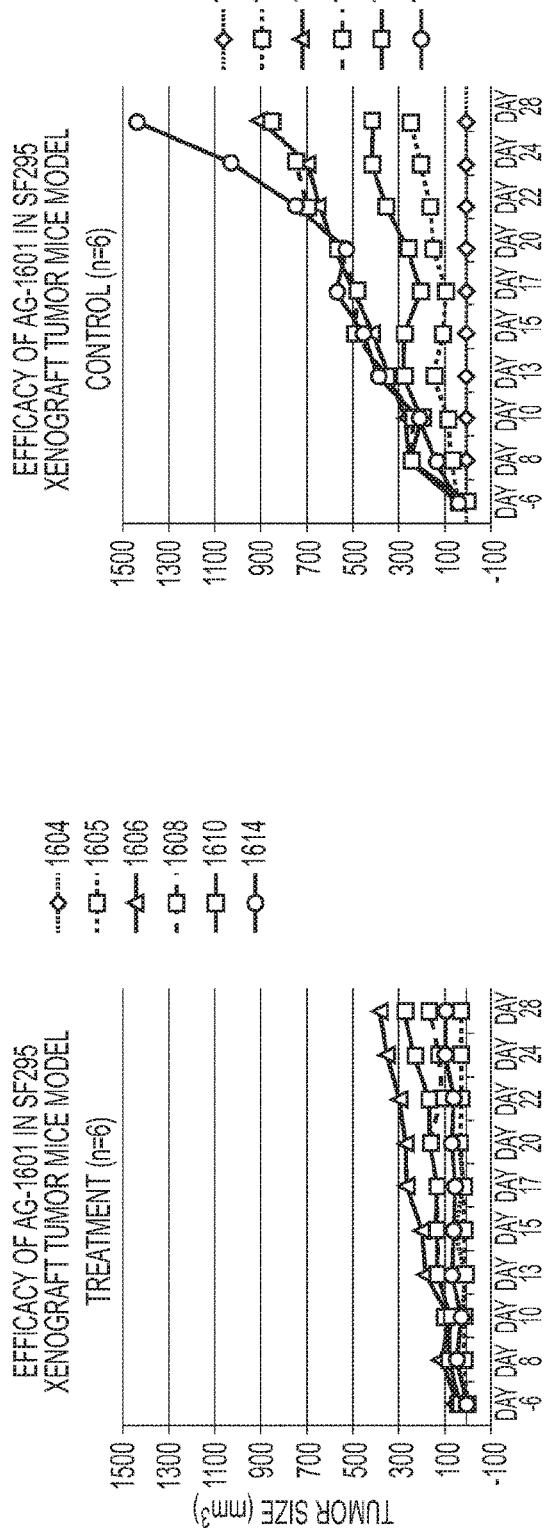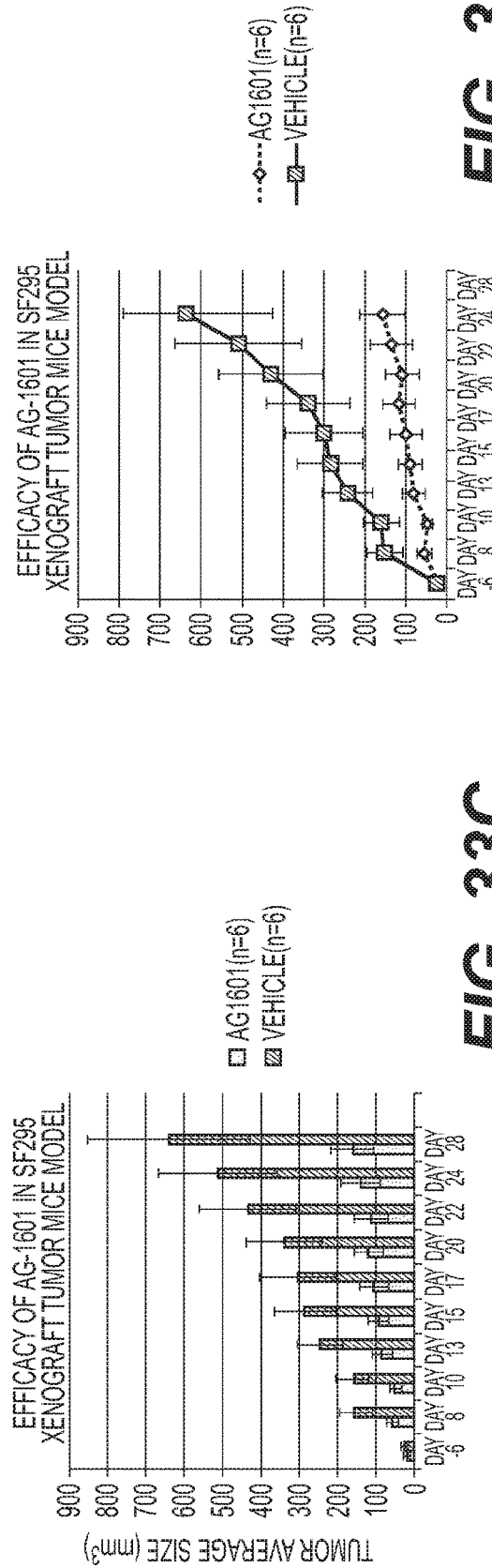

COMPOSITIONS AND METHODS FOR THE DIAGNOSIS, TREATMENT AND PREVENTION OF NEOPLASTIC AND NEUROLOGICAL DISORDERS

REFERENCE TO RELATED APPLICATIONS

This application is a National Stage submission under 35 U.S.C. § 371 of International Application No. PCT/US2019/39481 filed Jun. 27, 2019, which claims priority to U.S. Provisional Application No. 62/691,267 filed Jun. 28, 2018, the entirety of each of which is incorporated by reference.

BACKGROUND

1. Field of the Invention

The invention is directed to compositions and methods for the diagnosis, treatment and prevention of various forms of cancer. In particular, the invention is directed to compositions and methods comprising inhibitors or regulators of PC4 expression, activity and/or function.

2. Description of the Background

Current cancer therapeutics, including small molecules and biologics, target either cell surface molecules or cytoplasmic proteins. Inhibition of these targets can result in the initiation of cell apoptosis while allowing the nuclear DNA to remain intact, a pre-requirement of cancer recurrence. Therefore, therapies that target nuclear proteins, especially proteins involved in chromatin structure and DNA repair may have the potential to block apoptosis reversal and reduce recurrence rates.

Lung cancer is a leading cause of cancer related mortality in the United States with more deaths directly attributable to the disease than breast, prostate, and colorectal cancer combined. It was estimated that 158,040 Americans died from lung cancer in 2015. There are two main types of lung cancer. About 85% to 90% of lung cancers are non-small cell lung cancer (NSCLC) with the remainder being small cell lung cancer (SCLC). These types of lung cancer are treated very differently.

NSCLC has been classified as an orphan disease with clear unmet medical needs for quicker regulatory path. Despite the orphan disease status, the size of patient population with NSCLC is significant. The current treatment for NSCLC includes surgery and radiation for early stage disease and chemotherapy for stage IV metastatic (40%) or stage III locally advanced (30 to 40%) disease. Recent pipelines have been focused on target protein factors involved in tumor angiogenesis pathways including the members of the VEGFR, EGFR and tyrosine kinase families.

The human transcriptional positive cofactor 4 (PC4, also known as p14, p15, Sub1 homolog, etc.) is a single-stranded DNA-binding protein of 127-amino acid residues with serine-rich regions near the N-terminus. This cofactor has been cloned and identified as a general positive cofactor that could mediate transcriptional activation of many genes by directly interacting with many sequence- and cell-specific regulators [Ge and Roeder, (1994), Purification, cloning and characterization of a human coactivator, PC4, that mediates transcriptional activation of class II genes. Cell 78, 513-523; Kretzschmar, M. et al., (1994) A novel mediator of class II gene transcription with homology to viral immediate-early transcriptional regulators. Cell 78, 525-534]. The regulators mediated by PC4 include many nuclear hormone receptors, tumor suppressors, onco-proteins and other important factors that are essential for tumorigenesis and pathogenesis of other human diseases.

PC4 functions as an onco-protein and plays important roles in cell differentiation, development and pathogenesis of tumors (U.S. Pat. No. 8,076,061). The expression of PC4 is controlled by the tumor suppressor protein p53, which interacts with the PC4 protein itself at the transcription level. In addition, PC4 functions as a unique activator of p53 to regulate transcription of a number of genes involved in cell cycle, apoptosis, DNA repair and other cellular responses [Kishore A. H. et al., (2007) p53 regulates its own activator-transcriptional coactivator PC4: a new p53 responsive gene. Biochem. J. 406, 437; Banerjee, S. et al. (2004) General transcriptional coactivator PC4 activates p53 function. Mol. Cell Biol. 24, 2052-2062]. PC4 activities can be further regulated by posttranslational modification at least including phosphorylation and acetylation. Phosphorylation of PC4 inhibits its activity to interact with targeted activators and negatively regulates its co-activator function. Mass spectrometric analyses suggest that the in vivo hyperphosphorylation of PC4 is mainly mediated by casein kinase II and restricted to the N-terminal serine-rich region [Ge, H. et al., (1994) Phosphorylation negatively regulates the function of coactivator PC4. Proc. Natl. Acad. Sci. USA 91, 12691-12695]. Acetylation of PC4 is mediated by p300 and inhibited by phosphorylation [Kumor, P. B. R. et al., (2001) p300-mediated acetylation of human transcriptional coactivator PC4 is inhibited by phosphorylation. J. Biol. Chem. 276, 16804-16809].

There is a need to identify small molecules that regulate genes and proteins related to cancer and tumorigenesis, and for improved molecular diagnosis of malignancy. In addition, there is a need for improved methods of treating and preventing cancer with enhanced tumor specificity and reduced toxicity to normal cells and tissues.

SUMMARY

The present invention relates to agents that function to inhibit and/or prevent the development of cancers and, in particular, tumors and other disorders and in particular, compositions and methods comprising inhibitors or regulators of PC4 expression, activity and/or function.

One embodiment of the invention is directed to compositions comprising AG-1031, AG-1503, AG-1601 and/or combinations thereof. Preferably compositions further comprise a pharmaceutically acceptable carrier.

Another embodiment of the invention is directed to methods for treating or preventing a disorder comprising administering an effective amount of a pharmaceutical composition comprising AG-1031, AG-1503 and/or AG-1601 to a patient. Preferably the disorder is cancer and/or a neurological disorder and preferably the cancer is non-small cell lung carcinoma, a brain tumor or a glioma. Also preferably the neurological disorder is Alzheimer's disease. Preferably the effective amount of the pharmaceutical composition is therapeutically effective or prophylactically effective and the composition is administered intravenously, intramuscularly or orally.

Another embodiment of the invention is directed to vaccines for the prevention of disorders comprising AG-1031, AG-1503 and/or AG-1601. Preferably vaccines of the invention inhibit tumor formation, proliferation of cancerous cells, prevent metastatic disease, and/or neurological degeneration. These compounds are chiral molecules and exist as enantiomers with L and S isomeric forms. Compounds of the invention may contain both L and S isoforms, or be isolated as only L isoforms or only S isoforms.

Another embodiment of the invention is directed to methods of inhibiting or preventing tumor formation, proliferation of cancerous cells, metastatic disease, and/or neurological degeneration comprising administering vaccines of the invention to a patient in need thereof. Preferably administration is oral, intravenous or intramuscular. Also preferably, the vaccine may further comprise an adjuvant such as, for example, a compound containing aluminum. Alternatively, the adjuvant may be aluminum-free.

Other embodiments and advantages of the invention are set forth in part in the description, which follows, and in part, may be obvious from this description, or may be learned from the practice of the invention.

DESCRIPTION OF THE FIGURES

FIG. 3 Chemical structure of AG-1031 (9-methyl (I) and 13-methyl (II) trans-(+)-18-ethenyl-4,4a-dihydro-3,4-bis (methoxycarbonyl)4a,8,14,19-tetramethyl-23H, 25H-benzo [b]porphine-9,13-dipropanoate) shown as both L and S isoforms (Cas #: 129497-78-5 Verteporfin/Visudyne; MW: 718.794).

FIG. 4A Chemical structure of AG-1601 shown as both an L isoform (I; 3-(2,8,13,18-tetramethyl-3-(3-oxo-3-((3-phenylpropyl)amino)propyl)-12,17-divinylporphyrin-7-yl)propanoic acid); and an S isoform (II; 3-(3,7,12,17-tetramethyl-18-{3-oxo-3-[(3-phenylpropyl)amino]propyl)-8,13-divinylporphyrin-2-yl}propanoic acid (WJUS01-241-la; synthesized; MW: 679.86).

FIG. 5 Interference of API substances on PC4-DNA binding.

FIG. 6A Charts showing AG-1031 and AG-1503 inhibition of rat glioblastoma cell line C6.

FIG. 6B Charts showing AG-1031 and AG-1503 inhibition of human non-small cell lung cancer cell line H841.

FIG. 14A Open-field study of anxiety and activity of rats with glioma by AG-1503 as measured by distance of central locomotion.

FIG. 14B Open-field study of anxiety and activity of rats with glioma by AG-1503 as measured by total distance of locomotion.

FIG. 15 Efficacy of AG-1031 and AG-1503 to improve new object recognition.

FIG. 20A AG1601 improved cognitive impairment induced by Aβ42 in an open field and novel-object recognition (NOR) test. Time chart of the experiments. B. The number of entering into the center zone in open field test; C. Recognition index of short-term memory and D. The recognition index of long-term memory test.

FIG. 20B AG1601 improved cognitive impairment induced by Aβ42 in an open field and novel-object recognition (NOR) test. The number of entering into the center zone in open field test.

FIG. 20C AG1601 improved cognitive impairment induced by Aβ42 in an open field and novel-object recognition (NOR) test. Recognition index of short-term memory.

FIG. 20D AG1601 improved cognitive impairment induced by Aβ42 in an open field and novel-object recognition (NOR) test. The recognition index of long-term memory test.

FIG. 33A Efficacy of AG-1601 in SF295 xenograft tumor mice model (treatment at n=6).

FIG. 33B Efficacy of AG-1601 in SF295 xenograft tumor mice model (control at n=6).

FIG. 33C Efficacy of AG-1601 in SF295 xenograft tumor mice model (treatment at n=6).

FIG. 33D Efficacy of AG-1601 in SF295 xenograft tumor mice model (control at n=6).

DESCRIPTION OF THE INVENTION

PC4 is a general transcription cofactor that mediates transcription activation through diverse gene-specific and/or tissue-specific regulators. The active form of PC4 was found to be upregulated in the majority of cancer cell lines and primary tumors and PC4 expression levels were found to correlate with the degree of tumor malignancy (see U.S. Pat. No. 8,076,061). This regulatory molecule is involved in apoptosis, cell cycle progression, development, phosphorylation, proliferation, chromatin organization, DNA replication and repair, and other pathways related to cancer, neurodegenerative diseases and other disorders. Recent studies also have demonstrated that PC4 is one of the 48 common cancer markers characterized in human.

Figures 1, 2:
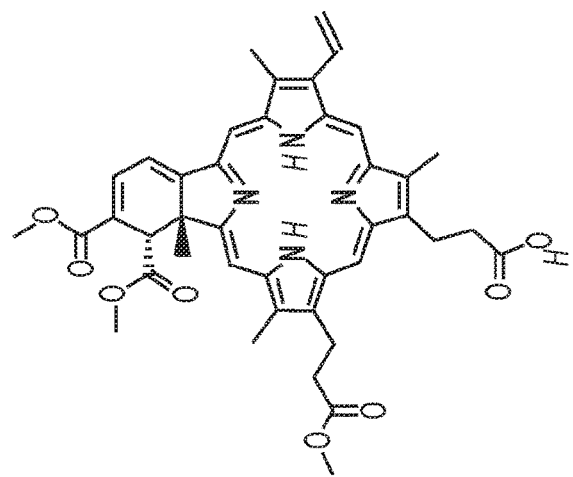
FIG. 1 Table of drug specifications and indications.
FIG. 2 Chemical structure of AG-1503 (only one isoform shown; (Cas #: 5522-63-4 Coproporphyrin III tetramethyl ester; MW: 710.83).

A number of molecules have been surprisingly discovered that inhibit PC4 activity both in vitro and in vivo (see FIG. 1). One surprising discovery is that the molecule AG-1031, currently used in photodynamic therapy and previously approved by FDA for non-oncology indication, specifically inhibits PC4 activity by blocking its double stranded DNA binding ability in vitro and in vivo inhibited non-small cell lung cancer (NSCLC) cell growth. In addition to inhibiting tumor growth in a mouse xenograft model derived from NSCLC cell line A549 after tumor formation, pre-injection of AG-1031 also effectively prevented tumor formation in a xenograft model. Furthermore, AG-1031 significantly inhibited glioma growth in a xenograft model derived from glioblastoma cell line C6 coupled with the recovery of memory loss and other activity loss.

Another surprising discovery is the molecule AG-1503 which is an analogue of AG-1031 with specific inhibitory activity on growth of glioma cell line C6, but not significant inhibitory activity on growth of NSCLC cell lines. Studies of xenograft model of C6 cell line indicated that AG-1503 had better activity for recovering memory loss and loss of other activities.

Another surprising discovery is the molecule AG-1601, a newly synthesized analogue of AG-1031. Studies indicate that, in addition to inhibiting growth of some NSCLC cell lines, this molecule had even better inhibitory activity on growth of glioma cells compared to AG-1503. The compositions and methods of the invention provide for a personalized medical approach not previously available for treating and/or preventing cancers, tumors and other medical disorders with new targets and new immune stimulating mechanisms.

AG-1503

AG-1503 (FIG. 2) is an analogue of AG-1031 and identified as a strong PC4 inhibitor and characterized as potential therapy for NSCLC, glioblastoma and Alzheimer's disease. AG-1503 may be used as a single therapy for NSCLC, glioma treatment and other cancers, when used alone or in combination with AG-1031, AG-1601 or other drugs. AG-1503 may be as in personalized medicine for NSCLC and or glioma, and/or as a supplement or vaccine to prevent occurrence of NSCLC and/or glioma. AG-1503 can be modified without decreasing functional activity by one or more modifications such as, for example, by substitution of addition of a hydrogen, hydroxyl group, linear or branched carboxy group, oxygen group, methyl group, or ethyl group, or by chemically coupling to similar molecules. In addition, AG-1503 is chiral and exist as enantiomers with L and S isomeric forms. Compounds of the invention may contain both L and S isoforms, or be isolated as only L isoforms or only S isoforms. The various chemical forms are all are referred to herein as AG-1503.

AG-1031

AG-1031 (see FIG. 3) is an FDA approved photodynamic (PD) drug for non-oncology indication. By using a high-throughput screen platform, AG-1031 was identified as a strong PC4 inhibitor and characterized for therapeutic efficacy against non-small cell lung cancer (NSCLC). In particular, AG-1031 may be used as a single therapy for NSCLC treatment alone or combined with AG-1503, AG-1601 or other drugs in a first line treatment for NSCLC and other cancers. AG-1031 may be as in personalized medicine for NSCLC and/or as a supplement or vaccine to prevent occurrence of NSCLC. AG-1301 can be modified without decreasing functional activity by one or more modifications such as, for example, by substitution of addition of a hydrogen, hydroxyl group, linear or branched carboxy group, oxygen group, methyl group, or ethyl group, or by chemically coupling to similar molecules. In addition, AG-1031 is chiral and exist as enantiomers with L and S isomeric forms. Compounds of the invention may contain both L and S isoforms, or be isolated as only L isoforms or only S isoforms. The various chemical forms are all are referred to herein as AG-1031.

AG-1601

AG-1601 (FIG. 4) is another analogue of AG-1031 that was newly synthesized. AG-1601 was identified as a strong PC4 inhibitor and useful as therapy for NSCLC, glioblastoma and Alzheimer's disease. The chemical structures of AG-1601 exists as both an L isoform (I; 3-(2,8,13,18-tetramethyl-3-(3-oxo-3-((3-phenylpropyl)amino)propyl)-12,17-divinylporphyrin-7-yl)propanoic acid); and an S isoform (II; 3-(3,7,12,17-tetramethyl-18-{3-oxo-3-[(3-phenylpropyl)amino]propyl)-8,13-divinylporphyrin-2-yl} propanoic acid (WJUS01-241-la; synthesized; MW: 679.86). AG-1601 as a single therapy for NSCLC and/or glioma treatment when used alone or in combination with AG-1031, AG-1503 or other drugs. AG-1601 as the personalized medicine for NSCLC and/or glioma companioned with diagnosis of PC4-positive patients. AG-1601 may be as in personalized medicine for NSCLC and or glioma, and/or as a supplement or vaccine to prevent occurrence of NSCLC and/or glioma. AG1601 showed better efficacy on Glioma cells in vitro than TMZ and Carmustine, shows efficacy on SF295 Xenograft tumor mouse model; and shows efficacy on C6 Xenograft tumor rat model. AG-1601 can be modified without decreasing functional activity by one or more modifications such as, for example, by substitution of addition of a hydrogen, hydroxyl group, linear or branched carboxy group, oxygen group, methyl group, or ethyl group, or by chemically coupling to similar molecules. Compounds of the invention may contain both L and S isoforms, or be isolated as only L isoforms or only S isoforms. The various chemical forms are all are referred to herein as AG-1601.

AG1601 and 3,3'-(3,7,12,17-tetramethyl-8,13-divinylporphyrin-2,18-diyl)bis(N-(3-phenylpropyl)propanamide) (referred herein as Compound B1) are prepared by coupling of starting material Ph-IX (3,3'-(3,7,12,17-tetramethyl-8,13-divinylporphyrin-2,18-diyl)dipropionic acid with 3-phenyl propylamine, using 1,1'-carbonyldiimidazole for activation. AG1601 and compound B1 can be purified by chromatographic method using a chloroform/methanol system to obtain isolable solid AG1601 and compound B1 in high chemical purity (>=95~97%).

The preparation method can include the following main steps:
a) activation of the carboxylic acid of the starting material, by 1,1'-carbonyldiimidazole in dimethylformamide/dichloromethane at ambient temperature for 1~3 hours to form carbonyl imidazole intermediate M.
b) dropwise addition of arylalkyl amines to above solution of intermediate M and continue stirring for 24~48 hours.
c) addition of water to above solution to precipitate out product and filter off solvent.
d) separation of crude product on silica gel column using chloroform/methanol (or ethanol) eluent to give AG1601 (slower migration on thin layer chromatography) and compound B1 (faster migration on thin layer chromatography).

The amides of any length of amines can be synthesized using this method. The method is particularly suited for rapid generation of analogs for biological screening. When intermediate M is formed, it can be divided to multiple portions for reaction of amines of substituents of different length and shape.

The method of the invention allows reaction to occur in commonly available solvents maintained in ambient conditions. The mono-amide and di-amide ratio can be controlled by amine quantity, to separate product mixture on silica gel column.

The method yields a mixture of mono- and di-amides which can be separated effectively. After chromatographic purification, pure (>=95%) mono- and di-amides can be used for in vitro and cellular screen.

The described method enables rapid generation of compounds with structural diversity and scalability for development quantities. For example, a compound library of amides can be prepared in the following procedure.

Ph-IX (3,3'-(3,7,12,17-tetramethyl-8,13-divinylporphyrin-2,18-diyl)dipropionic acid is first activated. Then it is divided into four equal portions and reacted with four different amines.

Step 1: To a Ph-IX (60 mg, 0.107 mmol) solution in 3 mL dry DMF (dimethyl formamide) was added CDI (1,1'-carbonyl diimidazole, 52 mg, 0.321 mmol).

Step 2: After being stirred for one hour at room temperature when the red color slightly faded, indicative of completion, the red liquid was dispensed via a syringe equally in four test tubes Step 3: 0.321 mmol of amine as shown in 3.1-3.4 below was added and stirred for 24 hours. Water was added to precipitate crude products.

Step 4: The crude product was loaded to a preparative Thin Layer Chromatography plate and eluted with a mixed solvent (chloroform:methanol=100:5) to separate di-amine from mono-amide isomers.

3.1: When 3-phenylpropylamine (45 µL, 0.321 mmol) was used in Step 3, AG1601 and compound B1 were obtained after chromatographic separation to give >95% (by viewing TLC plate under UV light, 253 nm). Yield: 28% (A, rf=0.4, mono-amide, 5 mg); 33% (B, rf=0.8, di-amide, 7 mg)

3.2 When propylamine (26 µL, 0.321 mmol) was used in Step 3, Compound C was obtained after chromatographic separation to give >95% purity (by viewing TLC plate under UV light, 253 nm). Yield: 17% (C, rf=0.5, di-amide, 3 mg)

3.3: When isopropylamine (28 µL, 0.321 mmol) was used in Step 3, Compounds D and E were obtained after chromatographic separation to give >95% purity (by viewing TLC plate under UV light, 253 nm). Yield: 35% (D, rf=0.5, di-amide, 5.7 mg), 29% (E, rf=0.8, mono-amide, 5 mg)

3.4.: When N,N-dimethylaminopropylamine (40 µL, 0.321 mmol) was used in Step 3, Compound F was obtained after chromatographic separation to give >90% purity (by viewing TLC plate under UV light, 253 nm). Yield: 26% (F, rf=0.15, di-amide, 5 mg)

Synthesis of methyl esters can be done by the following procedure.

To a Ph-IX (100 mg, 0.179 mmol) solution in 2 mL dry DMF (dimethyl formamide)/2 mL $CH_2CH_2$ (dichloromethane) was added DCC (N,N'-dicyclohexylcarbodiimide, 104 mg, 0.447 mmol), DMAP (4-dimethylamino pyridine, 12 mg, 0.1 mmol) and methanol (200 µL, 4.95 mmol, 13.8 equivalents to Ph-IX's acids). The mixture was stirred for three days at room temperature. The product mixture was poured in a separatory funnel and extracted with $CH_2Cl_2$ (25 mL)/15% NaCl solution (20 mL). The organic solvent was evaporated. The crude product was separated by column chromatography (20 g silica gel, eluent: 60 mL CHCl$_3$ and 1.5 mL methanol). The overlapped portion was separated again on a preparative TLC. Yield: Compound G, 39%, rf=0.25, 40 mg; Compound H, 57%, rf=0.6, 60 mg.

Compound G, 1H NMR (CDCl$_3$): 10.25 (s, 1H, C—H, ring), 10.20 (s, 1H, C—H, ring), 10.15 (s, 1H, C—H, ring), 10.11 (s, 1H, C—H, ring), 8.31 (dd, two sets, 2H, J$_1$=12 Hz, J$_2$=16 Hz, vinyl), 6.40 (dd, two sets, 2H, J=16 Hz), 6.22 (dd, 2 sets, 2H, J=12 Hz), 4.45 (m, two sets, 4H, CH$_2$), 3.65-3.75 (s, 5×CH$_3$), 3.30 (m, two sets, 4H).

Compound H, 1H NMR (CDCl$_3$): 10.30 (s, 1H, C—H, ring), 10.28 (s, 1H, C—H, ring), 10.19 (s, 1H, C—H, ring), 10.11 (s, 1H, C—H, ring), 8.23 (dd, two sets, 2H, J$_1$=12 Hz, J$_2$=16 Hz, vinyl), 6.41 (dd, two sets, 2H, J=16 Hz), 6.25 (dd, 2 sets, 2H, J=12 Hz), 4.42 (m, two sets, 4H, CH$_2$), 3.65-3.75 (s, 6×CH$_3$), 3.30 (m, two sets, 4H).

Synthesis of AG1601 and compound B1 in a large scale can be accomplished using the procedure outlined below.

To a Ph-IX (200 mg. 0.356 mmol) solution in 10 mL dry DMF (dimethyl formamide)/10 mL CH$_2$Cl$_2$ (dichloromethane) was added CDI (1, 1'-carbonyl diimidazole, 117.76 mg, 0.712 mmol). After being stirred for 0.75 hour at room temperature when the red color slightly faded, indicative of completion, 3-phenylpropylamine (63 mL, 0.445 mmol, 1.25 eq) in CH$_2$Cl$_2$ (15 mL) was slowly added over a period of 30 min. After 44 hours, TLC showed mono-amide as being a major spot. Water was added to decompose CDI. This procedure was repeated one more time using 330 mg (0.587 mmol) Ph-IX.

The combined crude product from above two reaction runs was subject to evaporation. After removal of dichloromethane, to the remaining liquid was added 150 mL aqueous (brine: water=1:2) to crush out a solid. After column chromatography (62 g silica gel), AG1601 (mono-amide) (388 mg. 61%) and compound B1 (di-amide) (64 mg. 8.5%) were obtained. A portion that contained both AG1601 and compound B1 (70 mg. ~9%) was also obtained.

AG1601. 1H NMR (DMSO-d$_6$): 10.30-10.40 (ms, 4H, ring), 8.60 (dd, two sets, 2H, J$_1$=12 Hz, J$_2$=16 Hz, vinyl), 7.30 (m, 1H, NHCO), 6.70-6.90 (m, 5H, Ph), 6.50 (dd, two sets, 2H, J=16 Hz), 6.25 (dd, 2 sets, 2H, J=12 Hz), 4.43 (m, two sets, 4H, CH$_2$), 3.80-3.78 (s, 2×CH$_3$), 3.65-3.70 (s, 2×CH$_3$), 3.30 (m, two sets, 4H), 3.01 (m, 4H, NCH$_2$ and CH$_2$Ph), 1.80 (m, 2H, C—CH$_2$—C); MS: Electrospray ionization positive mode: [M+1]+=680.4; High resolution MS confirms M+1=680.3601, formula: C$_{43}$H$_{46}$N$_5$O$_3$.

Compound B1. 1H NMR (DMSO-d$_6$): the spectrum has poor resolution and only estimation is offered here: 10.10-10.30 (s, 4H, C—H, ring), 8.30 (dd, two sets, 2H, J$_1$=12 Hz, J$_2$=16 Hz, vinyl), 6.70-6.90 (m, 10H, Ph), 6.70 (dd, two sets, 2H, J=16 Hz), 6.50 (dd, 2 sets, 2H, J=12 Hz), 4.43 (m, two sets, 4H, CH$_2$), 3.80-3.78 (s, 2×CH$_3$), 3.65-3.70 (s, 2×CH$_3$), 3.10 (m, two sets, 4H), 3.01 (m, 8H, NCH$_2$ and CH$_2$Ph), 1.50-80 (m, 4H, C—CH2-C).

MS: Electrospray ionization positive mode: [M+1]+=797.5; High resolution MS confirms: M+1=797.5453, formula: C$_{52}$H$_{57}$N$_6$O$_2$.

One embodiment of the invention is directed to compositions comprising small molecules that inhibit or regulate PC4 expression and/or activity. As the onco-protein PC4 plays an important role in oncogenesis with respect to many types of human cancers and tumors, regulation of PC4 expression results in suppression and/or inhibition of the proliferation of cells including cancer cells and metastatic diseases. Preferably, the compositions of the invention are formulated for treating or preventing cancers directly or indirectly by decreasing cellular PC4 level and/or inhibiting PC4 function. Preferred compositions of the invention comprise analogs and derivatives of compounds that inhibit or regulate PC4 expression and/or activity. Preferred PC4 inhibitors include, for example, AG-1031 (Verteporfin/Visudyne), AG-1503 (coproporphyrin III tetramethyl ester), AG-1601 and combinations thereof. Compositions of the invention treat or prevent a variety of disorders including but not limited to cancers, malignancies, tumors, neurological disorders and Alzheimer's disease. Compositions of the invention offer particular appeal as they are safe or and effective for short-term or long-term administration with minimal or no undesired side effects. These small molecules are preferable non-mutagenic (unlike chemotherapeutic agents) and not cytotoxic, but have a high potency for the treatment and/or prevention of one or more diseases and disorders. Certain small molecules identified are already FDA-approved for other medical indications with known safety profiles, whereas others are otherwise new and previously unknown. Analogs and derivatives include small molecules of the invention that have conservative substitutions, additions or deletions. A conservative substitution, addition or deletion includes, for example, the additional or deletion of a methyl group or an aldehyde group, or a non-functional marker or labeling compound.

Another embodiment of the invention is directed to pharmaceutical composition comprising small molecules of the invention. Pharmaceuticals compositions comprise small molecules of the invention in combination with pharmaceutically acceptable carriers and salts and may be aqueous or freeze dried. Pharmaceutically acceptable carriers include, for example, water and other aqueous solutions, oils, fatty acids, saccharides, carbohydrates and salts, and may be liquids, gels or solids such as powders, capsules or tablets that are formulated for direct administration or timed-release administration to a patient.

Another embodiment of the invention is directed to methods for the treatment of diseases and disorders comprising administrating a therapeutically effective amount of the compositions of the invention to a patient. Diseases and disorders that are treated with compositions of the invention include cancers such as, but not limited to lung cancer, bladder cancer, colon cancer, breast cancer, endometrial cancer, thyroid cancer, small bowel cancer, ovary cancer, and other malignancies, and Alzheimer's diseases and complications. Patients include, but are not limited to mammals such as humans (e.g., adults, adolescents, children, infants), primates, and domestic animals. Administration may be parenteral or nonparenteral, but is preferably oral, intramuscular or intravenous. Treatment may be for short periods of time (e.g., pulsed or continuous), for a short or long term, or continuous throughout the lifetime of the patient.

Compositions of the invention can be administered in effective amounts to a subject, either alone or in combination with one or more other treatments to effectively treat the cancer. An effective amount of a composition of the invention is that amount that is effective to reduce or eliminate the number of diseased cells and/or that amount to prevent recurrence of the disease. Preferably, the effective amount is that amount which is not harmful to the patient or that amount wherein any harmful side effects are minimized or otherwise outweighed by the beneficial effects of the composition to the patient. The effective dosage to be administered typically varies depending on the age or weight of the patient, and/or the severity of the disease.

Another embodiment of the invention is directed to pharmaceutical composition of the invention that, when administered to a patient, prevent pathogenesis of a disease or disorder. Such pharmaceutical compositions act as prevention drugs, immune stimulators, and/or vaccines preventing the disease or disorder such as, for example, cancers including but not limited to tumors and metastatic disease, neurological diseases and combinations thereof. Administration of compositions of the invention may be as a single prophylactically effective bolus, as multiple prophylactically effective doses and may include an adjuvant. The adjuvant may contain aluminum or, alternatively, the adjuvant may be aluminum-free. Administration may be parenteral or non-parenteral, but is preferably oral, intramuscular or intravenous.

In a further aspect, the present invention provides a kit comprising one or more compositions each comprising a therapeutically effective amount of one or more compounds of a compound of the disclosure, pharmaceutically acceptable salts thereof, solvates thereof, or prodrugs thereof, any combination thereof, and instructions to use the one or more compositions in treating brain cancer.

Compounds of the disclosure may be present in a composition and/or administered at an L to S isoform ratio, or an S to L isoform ratio, of approximately 1:1, 1:2 or more; 1:5 or more, 1:10 or more, 1:20 or more, 1:50 or more, or 1:100 or more.

Therapeutically effective comprises an amount of a compound of the disclosure that, when administered to a subject for treating the condition or disease herein (such as brain cancer), is sufficient to affect such treatment. The therapeutically effective amount will vary depending on the compound, the disease and its severity and the age, weight, physical condition, and responsiveness of the mammal to be treated.

Compounds of this disclosure may be administered to subjects such as, for example, preferably a mammal. Preferred mammals include, but is not limited to, guinea pigs, dogs, cats, rats, mice, hamsters, and primates, including humans.

Pharmaceutically acceptable indicates that the substance or composition is compatible chemically and/or toxicologically with the other ingredients comprising a formulation, and/or the mammal being treated therewith.

Pharmaceutically acceptable salts include, for example, salts that retain the biological effectiveness of the corresponding free acid or base of the specified compound and are not biologically or otherwise undesirable. Examples of pharmaceutically acceptable salts include those salts prepared by reaction of the compounds of the present disclosure with a mineral or organic acid or an inorganic base, such salts including, but not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present disclosure may include more than one acidic or basic moiety, the compounds of the present disclosure may include mono, di or tri-salts in a single compound.

A prodrug of the disclosure refers to a compound that may be converted under physiological conditions or by solvolysis to the specified compound or to a salt of such compound. The compounds and/or compositions of the present disclosure may be administered by various suitable routes. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. It will be appreciated that the route used may vary with, for example, the condition of the recipient. Where a compound is administered orally, it may be formulated as a pill, capsule, tablet, etc. with a pharmaceutically acceptable carrier or excipient. Where a compound is administered parenterally, it may be formulated with a pharmaceutically acceptable parenteral vehicle and in a unit dosage injectable form, as detailed below.

To use the compounds of the present disclosure for therapeutic treatment of mammals including humans, they can be formulated in accordance with standard pharmaceutical practice as a pharmaceutical composition. The pharmaceutical compositions of the invention are formulated, dosed and administered in a fashion, i.e., amounts, concentrations, schedules, course, vehicles and route of administration, consistent with good medical practice. Factors for consideration in this context include the disorder being treated, the mammal being treated, the clinical condition of the individual patient, the cause of the disorder, the site of delivery of the agent, the method of administration, the scheduling of administration, and other factors known to medical practitioners. The therapeutically effective amount of the compound to be administered will be governed by such considerations as well as identity and the amount of the compound being administered, and vice versa. The compounds of the present disclosure can be formulated into pharmaceutical dosage forms to provide an easily controllable dosage of the drug and to enable patient compliance with the prescribed regimen.

Pharmaceutical formulations of the compounds of the present disclosure may be prepared for various routes and types of administration. For example, two or more compounds of the present invention may optionally be mixed with pharmaceutically acceptable diluents, carriers, excipients or stabilizers in the form of a lyophilized formulation, a milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The formulations may be prepared using conventional dissolution and mixing procedures. For example, the bulk drug substance (i.e., a compound of the present disclosure or stabilized form of the compound) can be dissolved in a suitable solvent in the presence of one or more excipients.

The carrier, diluent or excipient used will depend upon the means and purpose for which the compound of the present disclosure is being applied. Solvents can be generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride, benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, argirune, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The formulations may also include one or more stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present disclosure or pharmaceutical composition thereof) or aid in the manufacturing of the pharmaceutical product (i.e., medicament). The active pharmaceutical ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). A "liposome" is a small-vesicle composed of various types of lipids, phospholipids and/or surfactant which is useful for delivery of a drug to a mammal. The components of the liposome are commonly arranged in a bilayer formation, similar to the lipid arrangement of biological membranes.

Sustained-release preparations of compounds of the present disclosure invention can be prepared. Suitable examples of sustained-release preparations include semipermeable matrices of solid hydrophobic polymers containing a compound of the present disclosure, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers.

The pharmaceutical compositions of the present disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose, any bland fixed oil may be employed including synthetic mono- or diglycerides. In addition, fatty acids such as oleic acid may likewise be used in the preparation of injectables.

Pharmaceutical compositions of the present disclosure suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The compositions of the invention may also be formulated in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder)

Suitable pharmaceutically-acceptable excipients for a tablet formulation include, for example, inert diluents such as lactose, sodium carbonate, calcium phosphate or calcium carbonate, granulating and disintegrating agents such as corn starch or alginic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be formulated in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the present disclosure may also be in the form of oil-in-water emulsions. The oily phase may be a vegetable oil, such as olive oil or *arachis* oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

Suppository formulations may be prepared by mixing the active ingredient with a suitable non-irritating excipient that is solid at ordinary temperatures but liquid at the rectal temperature and will therefore melt in the rectum to release the drug. Suitable excipients include, for example, cocoa butter and polyethylene glycols. Formulations suitable for vaginal administration may be presented as pessaries, tampons, creams, gels, pastes, foams or spray formulations containing in addition to the active ingredient such carriers as are known in the art to be appropriate.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for transdermal administration may be in the form of those transdermal skin patches that are well known to those of ordinary skill in the art.

Compositions for administration by insufflation may be in the form of a finely divided powder containing particles of average diameter of, for example, 30 μm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

The pharmaceutical composition (or formulation) for application may be packaged in a variety of ways depending upon the method used for administering the drug. For example, an article for distribution can include a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings. The formulations may also be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The compounds disclosed may also provide veterinary compositions comprising at least one active ingredient as above defined together with a veterinary carrier therefore. Veterinary carriers are materials useful for administering the composition and may be solid, liquid or gaseous materials which are otherwise inert or acceptable in the veterinary art and are compatible with the active ingredient. These veterinary compositions may be administered parenterally, orally or by any other desired route.

The amount of the compounds of the present disclosure that is combined with one or more excipients to produce a single dosage form will necessarily vary depending upon the subject treated, the severity of the disorder or condition, the rate of administration, the disposition of the compound and the discretion of the prescribing physician. Administration of the compounds or mixture of compounds of the present invention in some embodiments occurs between about 0.001 mg/kg of body weight to about 60 mg/kg of body weight per day. In another embodiment, administration occurs in an amount between 0.5 mg/kg of body weight to about 40 mg/kg of body weight per day. In some instances, dosage levels below the lower limit of the aforesaid range may be more than adequate, while in other cases still larger doses may be employed without causing any harmful side effect, provided that such larger doses are first divided into several small doses for administration throughout the day.

In another aspect, an article of manufacture, or kit, containing materials useful for the treatment described herein is provided. In one embodiment, the kit comprises a container comprising a compound of the present disclosure. Suitable containers include, for example, bottles, vials, syringes, blister pack, etc. The container may be formed from a variety of materials such as glass or plastic. The container may hold a compound of this invention or a formulation thereof which is effective for the treatment and may have a sterile access port. The kit may further comprise a label or package insert on or associated with the container. The package insert can contain instructions customarily included in commercial packages of therapeutic products, such as information about the indications, usage, dosage, administration, contraindications and/or warnings concerning the use of such therapeutic products.

Kits may include a composition of the present disclosure and a second pharmaceutical formulation. Kits may also comprise a container for containing the separate compositions such as a divided bottle or a divided foil packet, however, the separate compositions may also be contained within a single, undivided container. Kits may include directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

The following examples illustrate embodiments of the invention, but should not be viewed as limiting the scope of the invention.

EXAMPLES

Example 1

A number of small molecules were incubated with PC4 protein and DNA binding assessed. Only the small molecule identified as 31 (AG-1031) showed significant interference of PC4-DNA binding (see FIG. 5).

Example 2

Rat glioblastoma cell lines C6 (A) and human non-small cell lung cancer cell line H841 (B) were grown in the proper medium and treated with different concentration of drug candidate AG-1031 (P) and AG-1503 (#3). Cell growth rate was calculated based on the number of live cells as compared to concentration in M of selected small molecules of the invention (see FIGS. 6A and 6B).

Example 3

Figure 7:
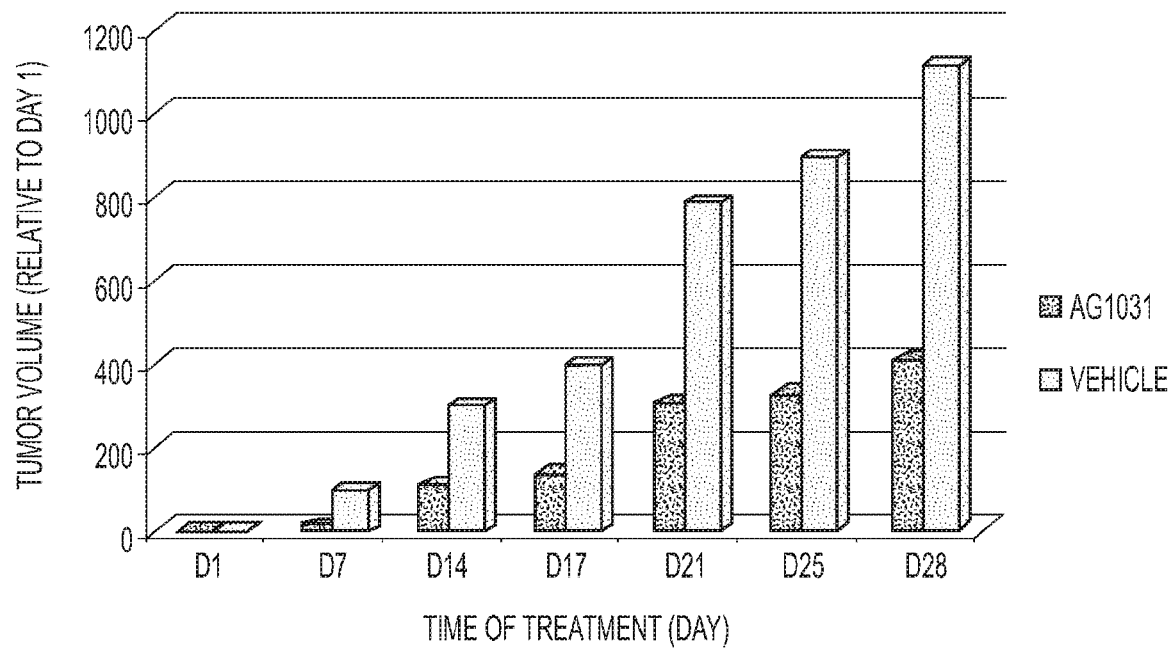
FIG. 7A histogram showing AG-1031 inhibition of growth of NSCLC tumor.

Mice were treated with AG-1031 (20-40 µg/mice) every other day via IP injection after A549 inoculate to the SHO mice treatment and followed for up to 28 days. Results are shown in FIG. 7.

Example 4

Figure 8:
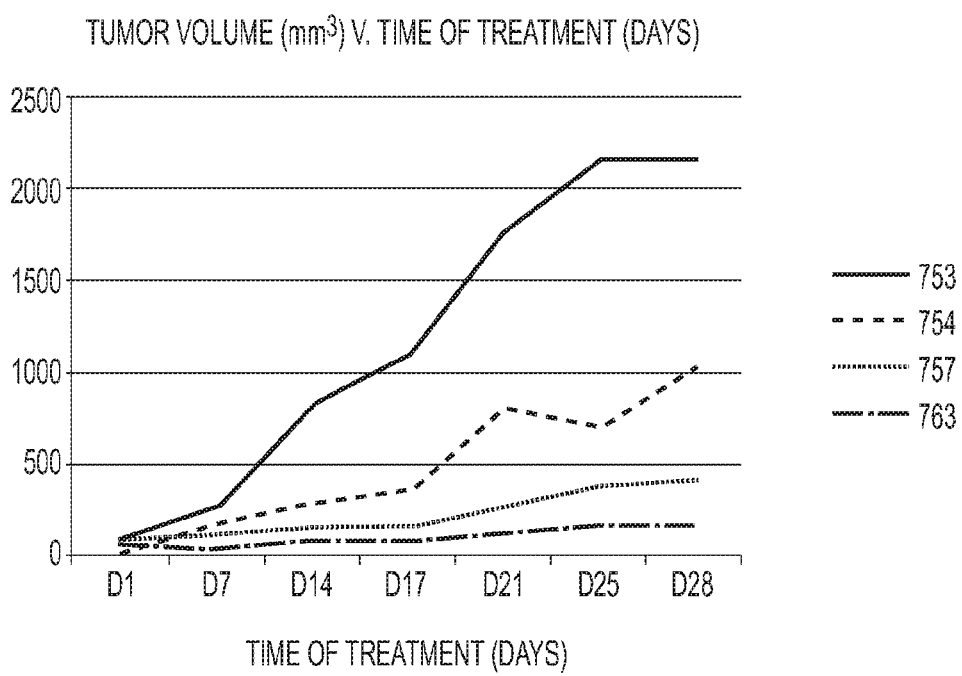
FIG. 8 Chart showing AG-1031 inhibition of growth of NSCLC tumor.

Tumor volume was measured during treatment of NSCLC cells with AG-1031 over 28 days. The results show that AG-1031 inhibits growth of NSCLC tumor cells (see FIG. 8).

Example 5

Figures 9, 10:
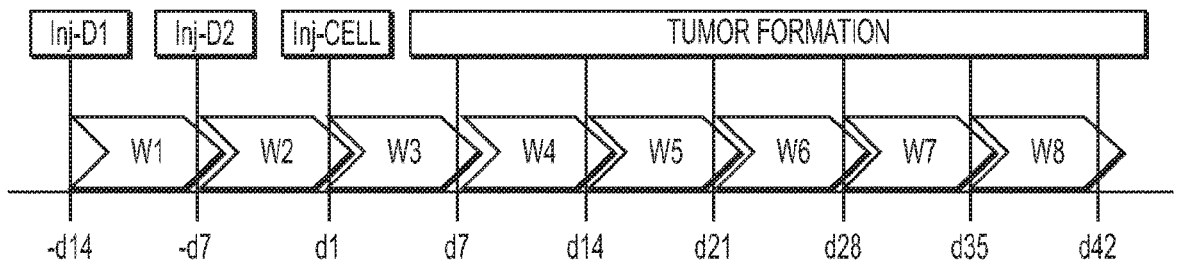
FIG. 9 Progressive steps in the use of AG-1031 as a vaccine against NSCLC.
FIG. 10 Growth results after administration of AG-1031 showing prevention of NSCLC formation.

AG-1031 was injected into mice two weeks before injection of tumor cell (see FIG. 9). As compared with a control group, tumor volume of the AG-1031 treated group was reduced from 302.9 mm$^3$ to 69.0 mm$^3$ demonstrating that AG-1031 prevents NSCLC formation in vivo (see FIG. 10).

Example 6

Figure 11A:
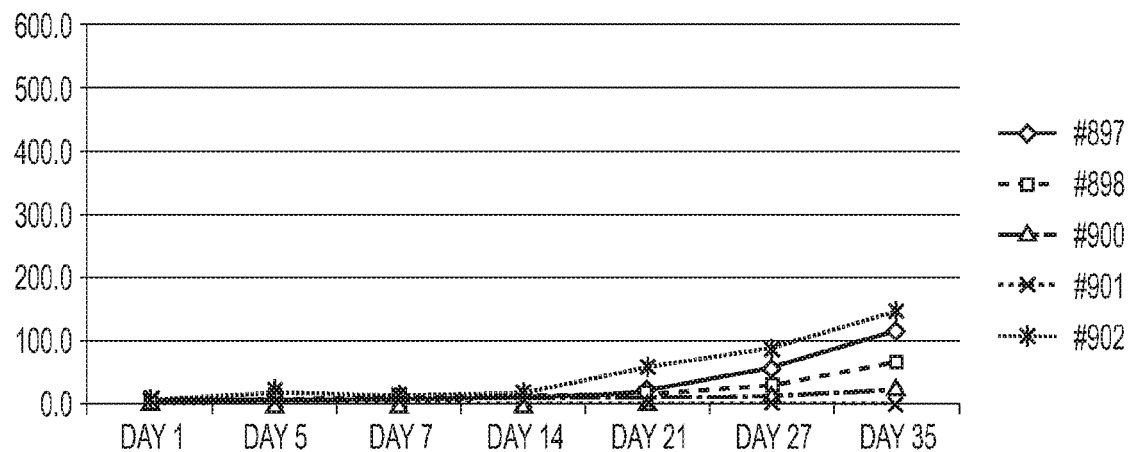
FIG. 11A Assessment of AG-1031 effect on tumor growth in A549 xenograft mice after vaccination with one of compounds 897-902.
Figure 11B:
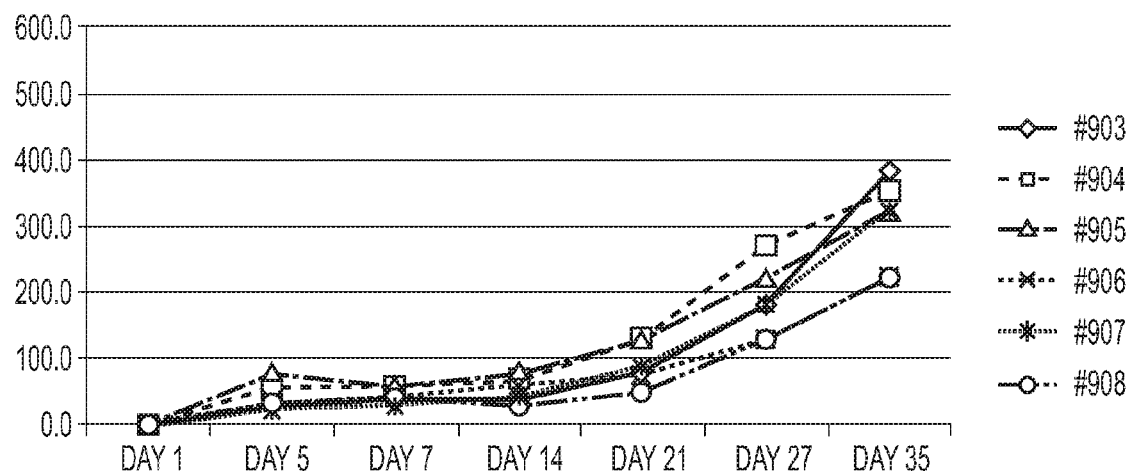
FIG. 11B Assessment of AG-1031 effect on tumor growth in A549 xenograft mice after vaccination with one of compounds 903-908.

Tumor volume was measured for 35 days after administration of AG-1031 to xenograft mice. As shown in FIGS. 11A and 11B, AG-1031 substantially reduces tumor volumes in treated mice.

Example 7

Figure 12:
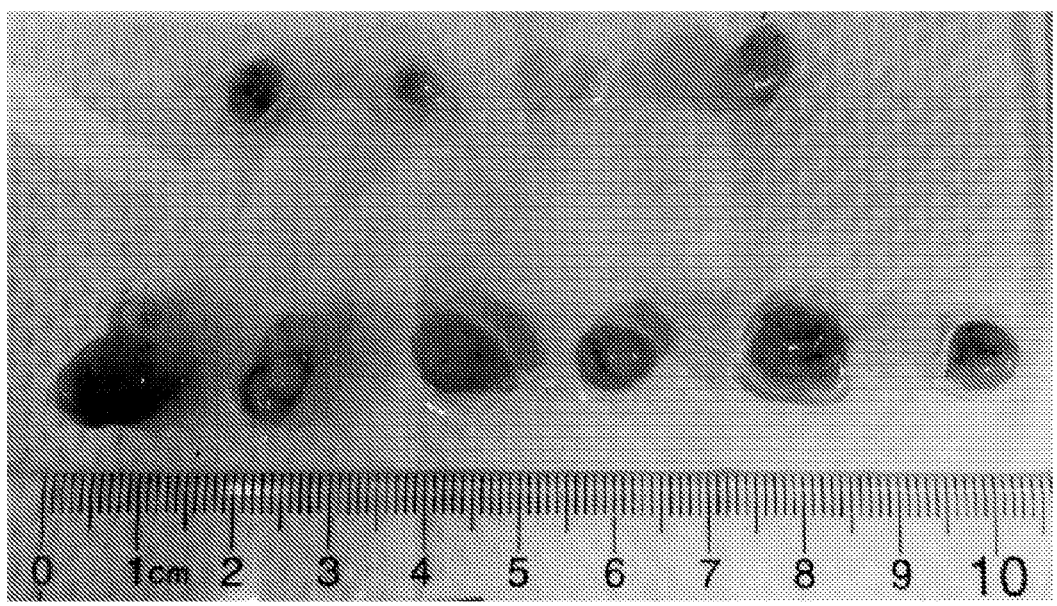
FIG. 12 Assessed vaccine effect of AG-1031 on tumor growth in A549 xenograft mice (vaccine group—top; control group—bottom).

FIG. 12 shows the actual tumor sizes in AG-1031 vaccinated mice as compared to the untreated control group as measured charted.

Example 8

Figure 13:
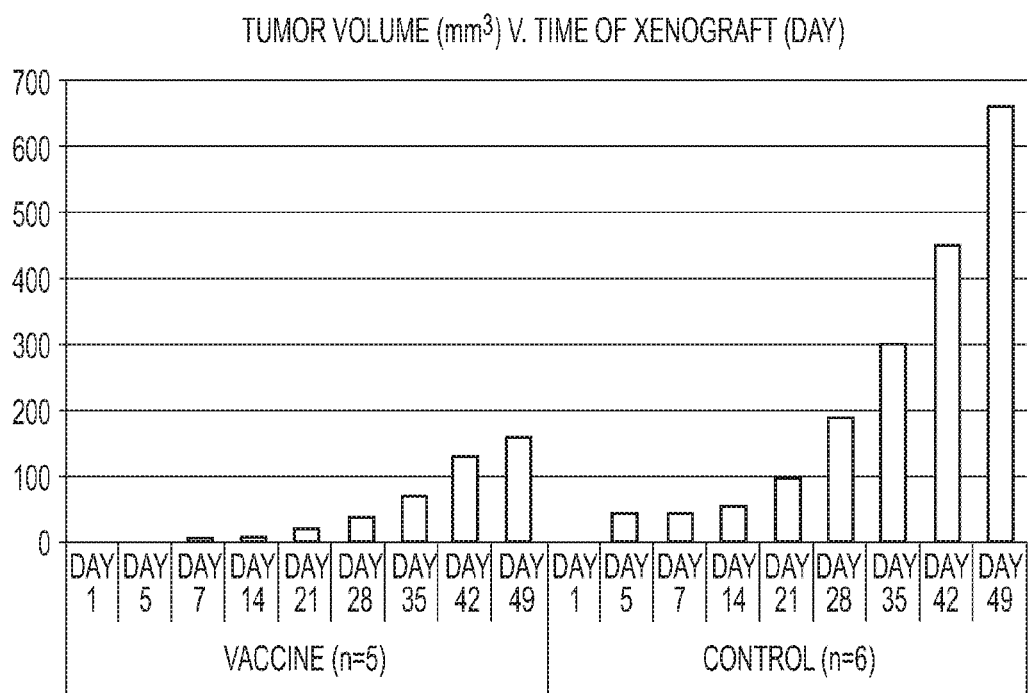
FIG. 13 Assessment of AG-1031 effect on tumor growth in A549 xenograft mice.

IP inject with AG-1031 40 µg/mice, once a week (×2) before A549 cells inoculate to the SHO mice. Assessment of AG-1031 effect on tumor growth in A549 xenograft mice. Results are shown in FIG. 13.

Example 9

Open-field study shows improvement of anxiety and activity of rats with glioma that have been treated with AG-1503 (see FIGS. 14A and 14B).

Example 10

Both AG-1031 and AG-1503 showed efficacy to improve ability of new object recognition (see FIG. 15).

Example 11

Figure 16B:
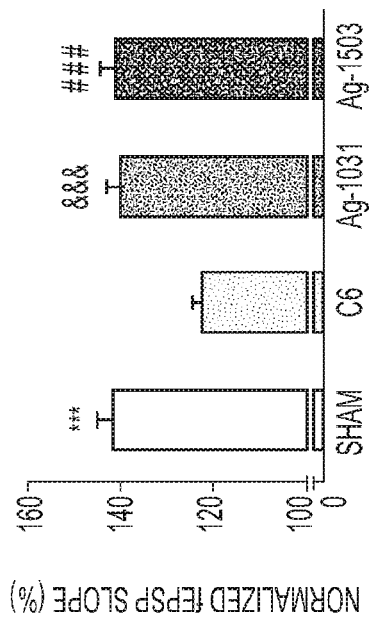
FIG. 16B Electrical Physiology test of study and memory capability as measured by actual percent.
Figure 16A:
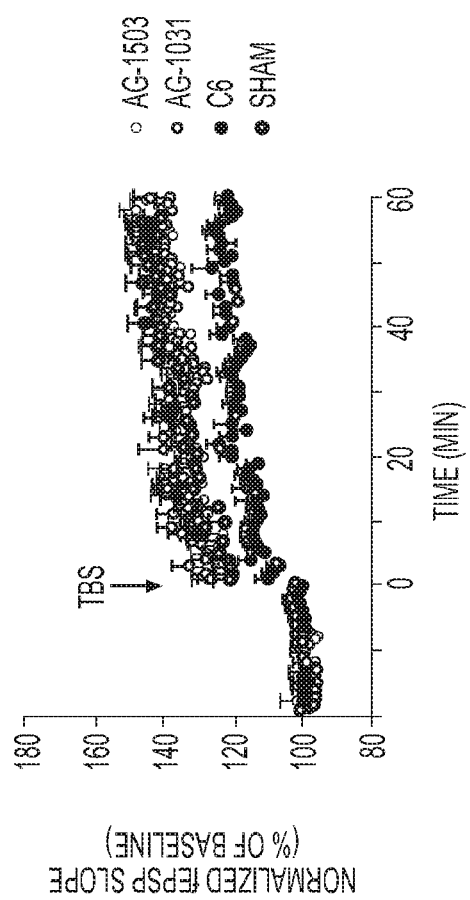
FIG. 16A Electrical Physiology test of study and memory capability as measured by percent of baseline.

Electrical Physiology test shows improvement of study and memory capability (see FIGS. 16A and 16B).

Example 12

Figure 17B:
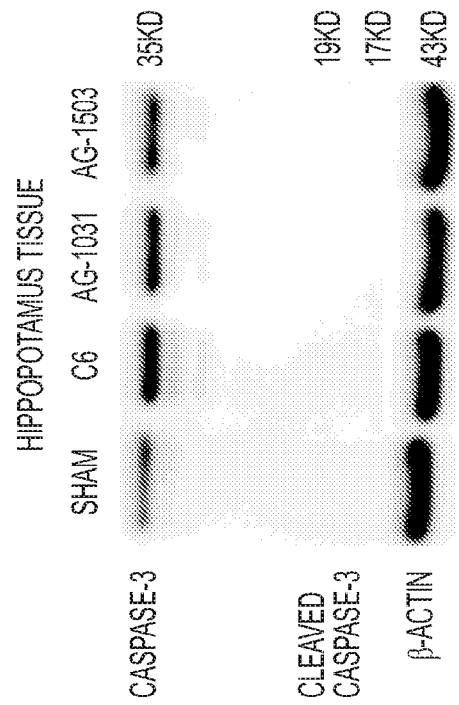
FIG. 17B Western Blot of apoptosis-related proteins in hippopotamus tissue.
Figure 17A:
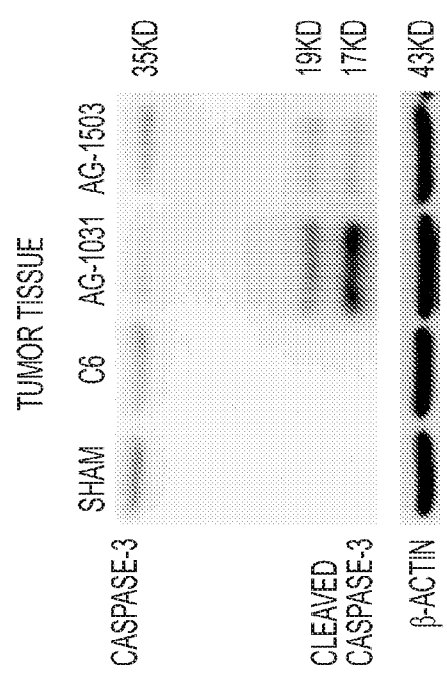
FIG. 17A Western Blot of apoptosis-related proteins in tumor tissue.

Western Blot of apoptosis-related proteins in (A) tumor tissue and (B) hippopotamus tissue (see FIGS. 17A and 17B).

Example 13

Figure 18A:
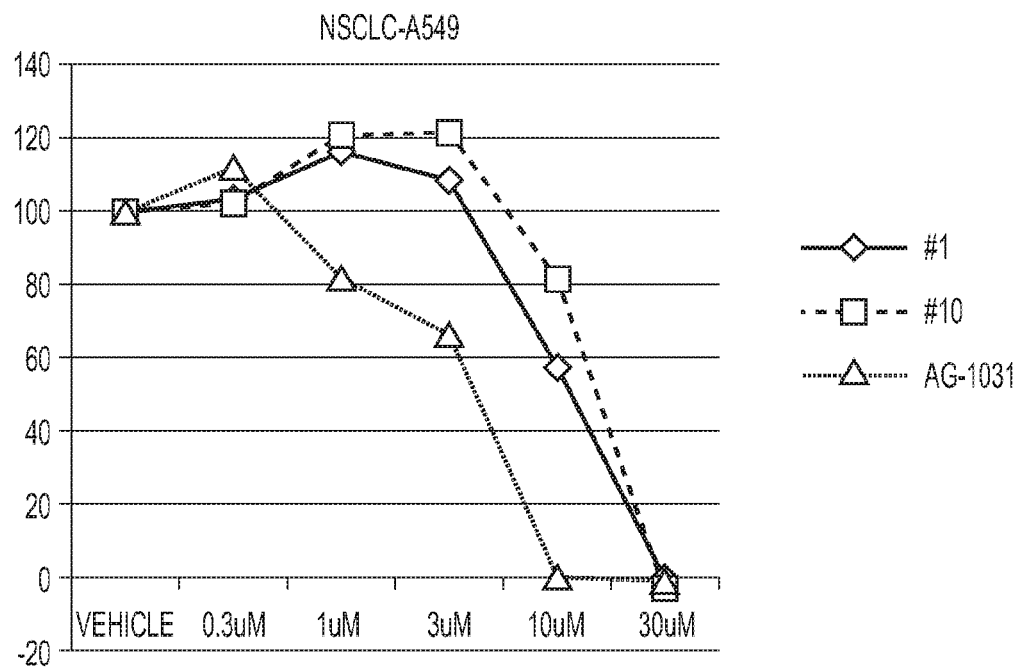
FIG. 18A Screening of new compounds identified AG-1601 on NSCLC-A549 cells.
Figure 18B:
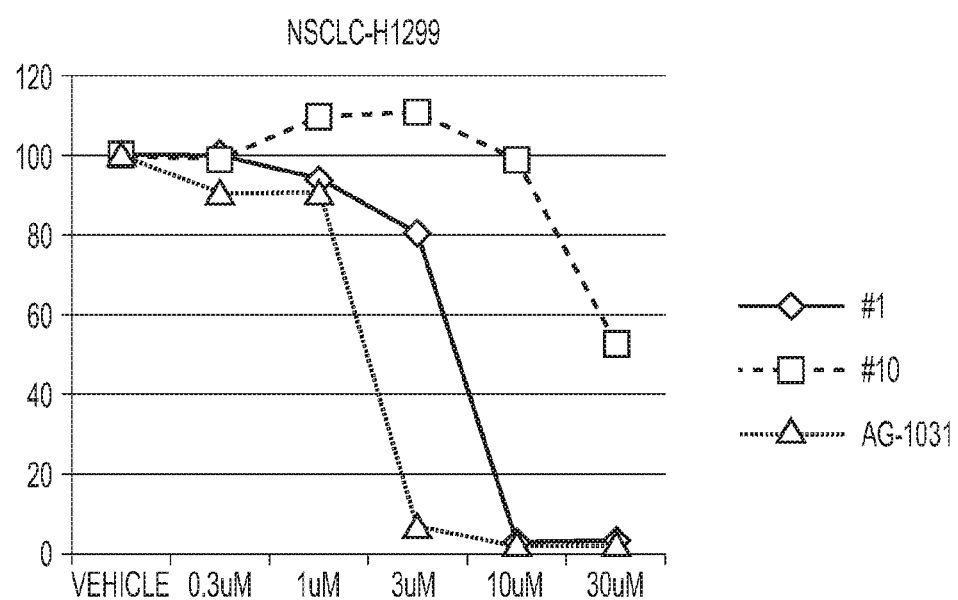
FIG. 18B Screening of new compounds identified AG-1601 on NSCLC-14299 cells.

Screening of new compounds identified AG-1601 on NSCLC-A549 and NSCLC-14299 cells (see FIGS. 18A and 18B).

Example 14

Figure 19A:
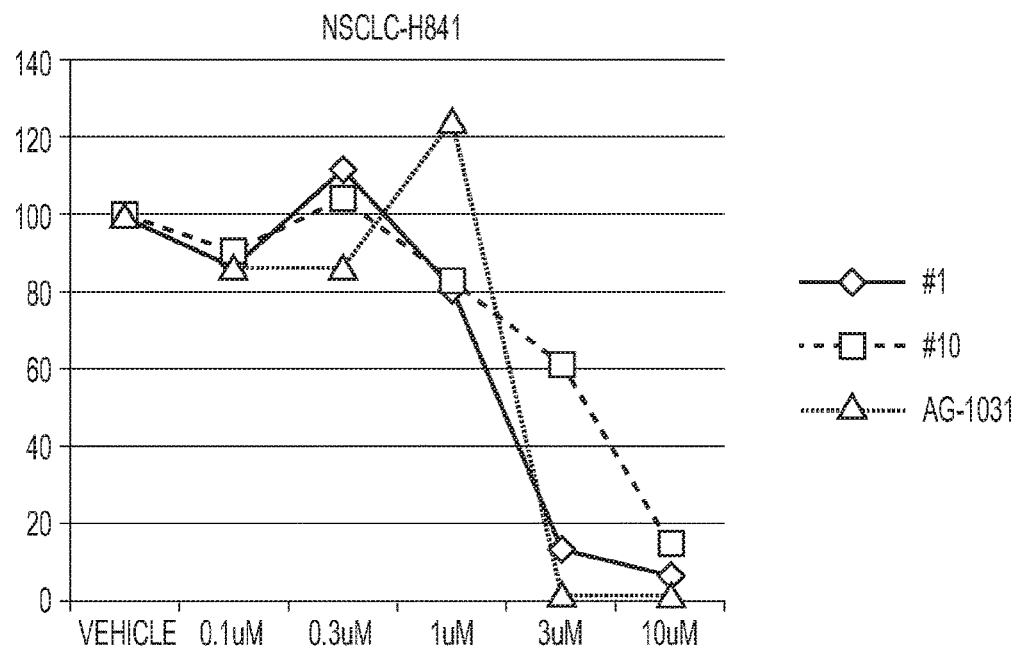
FIG. 19A Screening of new compounds identified AG-1601 on NSCLC-H841 cells.
Figure 19B:
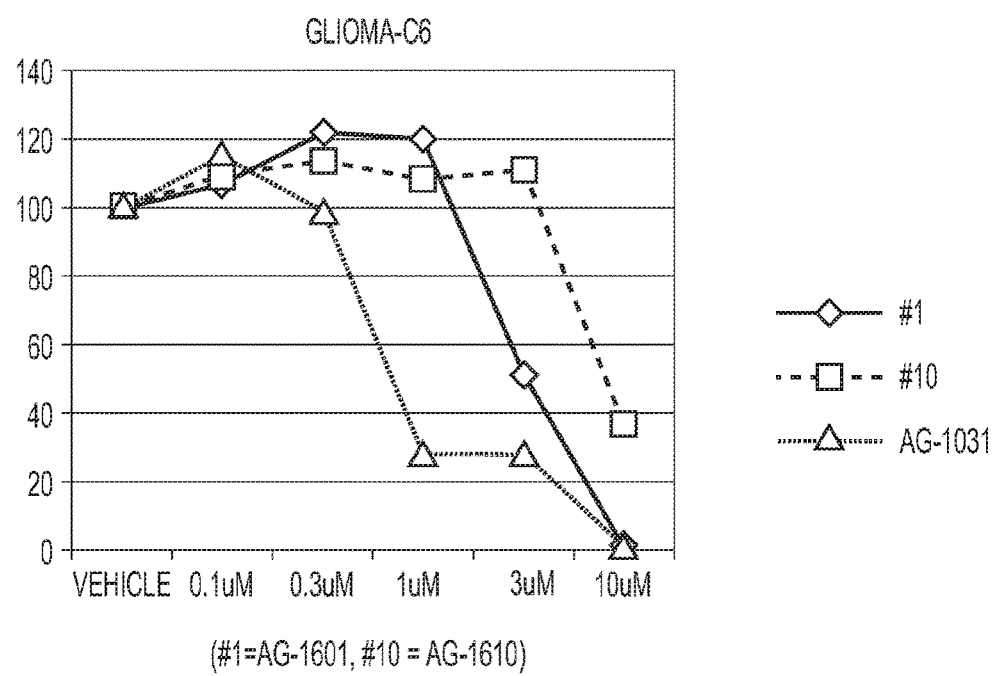
FIG. 19B Screening of new compounds identified AG-1601 on glioma C6 cells.

Screening of new compounds identified AG-1601 and AG-1610 (as less active variant of AG-1601) on NSCLC-H841 cells (FIG. 19A) and glioma C6 cells (FIG. 19B).

Example 15

AG-1601 is a small molecule and was dissolved in DMSO at 5 mg/ml and stored at 4C, and diluted to the final concentration of 1 mg/mL with PBS before use. The basic TEVP buffer contained 10 mM Tris. HCl (pH 7.5), 50 mM NaF-50, 5 mM EDTA, 5 mM EGTA, 1 mM benzamidine, 1 mM PMSF, 2 µg/ml leupeptin and pepstatin at 2 µg/ml.

Adult male Sprague-Dawley (SD) rats (weighing 200-250 g) were provided by the Laboratory Animal Center, Academy of Military Medical Science of People's Liberation Army. Rats were housed under the controlled conditions (25±2° C.; 12-h light/dark cycle) with free access to food and water in the Medical School of Nankai University and acclimated for one week before the experiments. All experimental procedures were approved by the "Nankai University" and performed according to the guidelines of the Guide for the Care and Use of Laboratory Animals published by the National Institutes of Health with efforts were made to minimize the number and suffering of animals used for the experiments.

Aβ1-42 (Sigma-Aldrich, St. Louis, MO, USA;) was dissolved in double-distilled water at the concentration of 5 μg/μl, and incubated at 37° C. for one week before surgery. The rats were randomly divided into four groups as Sham (n=8), Sham+AG-1601 (n=8), Aβ1-42 (n=8) and Aβ1-42+AG-1601 (n=8). The Alzheimer's disease rat models were established by intracerebroventricular (i.c.v.) injection of Aβ1-42 aggregates. The animals were anesthetized with intraperitoneal injection of pentobarbital sodium (50 mg/kg) and placed in a stereotaxic apparatus (Narishige, Japan). The head skin of the rat was opened and two small holes were drilled on both sides of skull following the coordinates: 0.8 mm posterior to bregma, +1.4 mm lateral to sagittal suture, 4.0 mm beneath the surface of brain. Aβ1-42 (2.0 μl per side) was injected bilaterally into the lateral ventricles through micro-syringe. The needle was taken out after 5 minutes of the injection to ensure the aggregates were infused completely. Rats in the Sham group underwent the same operational process, but same volumes of double-distilled water were injected instead of Aβ1-42. After surgery, all rats were injected with penicillin (100,000 U) in the hindquarter muscle to prevent infection. The animals of Sham+AG-1601 and Aβ1-42+AG-1601 groups were intravenous injection with AG-1601 (1 mg/kg), while the same volume vehicle was implemented for the other groups every day for 14 days after one week of the postoperative recovery.

The open field test was carried out to evaluate locomotor activity and exploratory behavior. This test was conducted as described previously with little modifications (Sugita et al., 2015). The open field test consists of a circular apparatus (80 cm in diameter, 30 cm high). The circular apparatus was divided into the center zone (30 cm in diameter in the middle of the arena) and the concentric outer circle zone. Rats were placed individually in the outer circle of the apparatus and allowed to explore freely for 5 min. The path of each rat was tracked by a camera-driven tracker system (Ethovision2.0, Noldus, Wagenigen, Netherlands). The number of entries into the center zone, the total distance and the traveling speed during the testing were analyzed.

The short- and long-term memory functions of the animals were evaluated by using the NOR test, which were carried out after the open field test. The experiment was performed in the same arena used for the open field test as previously described (Sugita et al., 2015). This test included four different stages: habituation stage, training stage, short-term memory test stage and long-term memory test stage. The open field test was thus used as the phase of habituation in the present study. Twenty-four hours after open field exploration, two identical plastic bottles (objects A1 and A2) were placed on diameter of the open field. The spacings of objects were equidistant from each other and from the wall. In training stage, rats were allowed to explore the arena freely for 5 min. After 1h, the short-term memory test was commenced. Rats explored the field for 5 min in the presence of one of the familiar objects was replaced with a novel object B (a triangular cube). A recognition index was calculated by the percentage of TB/(TA+TB) (TA: time spent exploring the familiar object A; TB: time spent exploring the novel object B). The long-term memory test was given 24 h after training, rats were allowed to explore the arena for 5 min in the presence of the object A and a third novel object C (a metal tube, and the recognition index was evaluated as same as that in the short-term memory test. A recognition index of 50% in the training phase indicates the chance level and a higher recognition index of the test stage reflects preferable object recognition memory. All objects used in this experiment should be too heavy for rats to move, and they were cleaned with 70% ethanol solution between every trial. The animal's behavior was captured by the video camera.

The rats were placed in the stereotaxic apparatus after intraperitoneal injection of 30% urethane (0.4 g/kg Sigma-Aldrich, St. Louis, MO, USA). According to our former protocols (Gao et al., 2015) the appropriate incision on the scalp was cut to expose the skull and a small hole was drilled. A bipolar stimulating electrode was placed in the Schaffer collateral pathway (4.2 mm posterior to the bregma, 3.8 mm lateral, 2-3.5 mm inferior to the dura), and a monopolar recording electrode was implanted ipsilaterally the CA1 region (3.5 mm posterior to the bregma, 2.5 mm lateral, 1.5-2 mm inferior to the dura). The depth of both electrodes was optimized to acquire the proper amplitude of evoked potentials. Subsequently, a kind of single stimulus intensities were gradually increased from 0.1-1 mA to determine the maximum field excitatory postsynaptic potential (fEPSP) slope, and the stimulus intensity that evoked 70% of maximum fEPSP slope was chosen to evoke fEPSPs before and after theta burst stimulation (TBS). A test stimulus was given every 30 s to record for 20 min as baseline. Then LTP was induced by TBS (30 trains of 12 pulses at 200 Hz) and recorded every 60s for 60 min. After that, low-frequency stimulation (LFS, 1 Hz for 15 min) was carried out to induce depotentiation (DEP) and the same single-pulse recording was continued every 60s for 60 min. The fEPSP slopes for the last 20 min of LTP were averaged and represented as the baseline of DEP.

Golgi-Cox staining method that performed according to the previously described protocol was used to determine the density of apical dendritic spines of the CA1 pyramidal cells in this study (Zhang et al., 2016). Briefly, the fresh brain tissue samples (n=3 each group) were removed from the anesthetized rats and were cut into coronal blocks containing the whole hippocampus. Then, the tissues were immediately placed into Golgi-Cox solution (5% potassium dichromate, 5% potassium chromate, and 5% solution of mercuric chloride) and held at room temperature away from light for 14 days. The Golgi-Cox solution was changed every 48h for 3 times in the meantime. After that, brain tissues were sectioned by vibratome (Leica-VT1000S, Germany). Slices (150 μm thickness) were transferred into 6% solution of sodium carbonate for 20 min. Thereafter, they were washed in distilled water and dehydrated with serial dilutions of alcohol (70%, 90%, 100%) and finally kept in the solution xylene for 20 min. Finally, the slices were covered with cover slips using resinous medium. The slides were allowed to dry at room temperature before observing under microscope (100×) for cytomorphological analysis. Six neurons in the CA1 region of hippocampus per animal were analyzed. The average dendritic spine density per 10 μm of dendritic length was calculated for each animal.

Three rats of each group were randomly selected to be sacrificed and their hippocampal tissues were immediately removed at 0° C. and stored at minus 80° C. For subcellular fractionation, 100- to 200-mg weight rat hippocampal tissue was used. The procedure has been described (Yang et al., 2017). The tissues were homogenized for 30 s in 500 μl TEVP buffer containing 320 mM sucrose and the homogenate was obtained. The homogenate (H) was centrifuged at 900×g for 10 min at 4° C., and the supernatant (S1) was centrifuged for 20 min at 10000×g at 4° C. to obtain the cytosolic/light membrane fraction (S2) and the crude synaptosomal fraction pellet (P2). The pellet was resuspended in TEVP buffer containing 35.6 mM sucrose solution and then centrifuged at 25,000×g for 20 min at 4° C. The supernatant was stored at minus 80° C. and referred as the synaptic vesicular fraction (LS1). The pellet, synaptic plasma membranes (LP1), was resuspended in TEVP buffer containing 1% Triton X-100 and centrifuged at 330,000×g for 30 min at 4° C. The supernatant referred as Triton X-100-soluble fraction (TSF) was stored at minus 80° C. The final pellet, the Triton X-100-insoluble fraction (TIF), was homogenized in TEVP buffer containing 1% SDS.

The concentration of every component was measured by the BCA protein assay kit (Beyotime Biotechnology, China). The components were finally boiled with 4× loading buffer at 100° C. for 15 min and stored at minus 80° C. for Western blot assay.

The total homogenate (H) and synaptosomal fractions were analyzed. Equal amounts of 20 μg from each sample were separated via 10% or 13% SDS-PAGE gels and subsequently transferred onto PVDF membranes (Millipore, USA). The membranes were blocked with 5% nonfat dry milk for 1 h at room temperature and then incubated with primary antibodies (Anti-synaptophysin, 1: 1000, Abcam; Anti-NR 2A, 1: 2000, Abcam; Anti-NR 2B, 1: 2000, Abcam; Anti-PSD-95, 1: 2000, Abcam; Anti-CREB, 1: 2000,Abcam; Anti-CREB phosphorylation, 1: 2000, Abcam; Anti-SIRT1, 1: 2000, Santa Cruz Biotechnology; Anti-β-actin, 1:5000, Santa Cruz Biotechnology) overnight at 4° C. Membranes were then incubated for 1 h at room temperature with horseradish peroxidase-conjugated secondary antibodies (Promega). After washing with TBST buffer, signals were visualized with the HRP substrate (Millipore, USA) and detected with a chemiluminescence kit (Tanon 5500, Tanon Science & Technology, China). The gray-scale value of protein band was quantified by NIH Image J program.

All data are expressed as the mean±SEM (standard error mean). The statistical analysis was processed by SPSS 19 software (Chicago, IL, United States). One-way analysis of variance (ANOVA) with LSD post-hoc test was applied to compare the data between groups. Statistical significance was set at $P<0.05$.

Example 16

The effect of AG-1061 on Aβ1-42-induced cognitive impairments was determined. The locomotion activities of rats were observed during the open field test. Comparing with Sham group, the Aβ1-42 group exhibited a significant decreased number of entries into the center zone ($P<0.01$). The number of entries into the center zone was increased significantly in Aβ1-42+AG-1061 group compared with that of Aβ1-42 group ($P<0.05$). Results showed that there was no significant difference in the total distance and the traveling speed between these four groups ($P=0.954$, $P=0.127$) indicating that all rats did not exhibit locomotor deficits.

NOR test is based on the spontaneous tendency of rodents to explore novel objects (Ennaceur and Delacour, 1989). Both the short- and long-term memory ability were detected by this test. In the training phase, rats of four groups spent the comparable time exploring the two identical objects, and the recognition index of every group was about 50% ($P=0.81$). In the short-term memory test stage, the recognition index was higher significantly in Sham group than the 50% chance level. However, Aβ1-42 group rats failed to differentiate the novel object from the familiar object in the short-term memory test, and the recognition index was lower significantly than the Sham group ($P<0.01$). Moreover, Aβ1-42+AG-1061 group showed a significant increase in recognition index compared with the Aβ1-42 group ($P<0.05$). The results of the long-term memory test showed the similar effect ($P<0.01$, $P<0.05$). The hippocampal synaptic plasticity in the CA1 region of rat was assessed to explain the neuroprotective effects of AG-1061 on Aβ1-42-induced cognitive impairments. After 20 min of stable baseline fEPSP recording. TBS was delivered to Schaffer collateral to induce LTP. The fEPSPs potentiated in the CA1 region were continuously recorded for 60 min. Then, LFS was administered 15 min to induce DEP. The last 20 min data of LTP and DEP were analyzed. The results revealed that the fEPSP slopes of LTP were reduced in Aβ1-42 group compared with that of Sham group ($P<0.001$). However, the suppressed LTP was augmented significantly by AG-1061 ($P<0.01$). There was also significant discernible effect on DEP. The data showed that Aβ1-42 injection significantly increased the fEPSP slopes of DEP ($P<0.001$), while the adverse effects were reversed effectively by AG-1061 treatment ($P<0.001$).

To determine the effect of AG-1061 on Aβ1-42-induced suppressions of LTP and DEP, the hippocampal synapse was fractionated and then assessed by Western blot assay. The synaptic and extrasynaptic positions were probed by NR2A, NR2B, PSD-95 and SYP. SYP was enriched in the TSF fraction finally. In contrast to SYP, the expressions of NR2A, NR2B and PSD-95 were enriched in the TIF fraction containing the postsynaptic density (PSD). It was found that Aβ1-42 injection reduced levels of NR2A, NR2B and PSD-95 in the H ($P<0.05$, $P<0.01$, $P<0.05$) and especially in the TIF fractions ($P<0.01$, $P<0.001$, $P<0.01$). Simultaneously, the expression level of SYP was decreased dramatically in the TSF fraction ($P<0.05$). However, NR2A, NR2B and PSD-95 levels were increased in the H ($P<0.05$, $P<0.05$, $P<0.01$) and the TIF fractions ($P<0.01$, $P<0.01$, $P<0.001$) in Aβ1-42+AG-1061 rats. In addition, the level of SYP in TSF fraction was also increased compared to that of Aβ1-42 group ($P<0.05$). These findings indicate that AG-1061 likely reverses LTP and DEP through upregulating the expression levels of synaptic proteins.

The loss of synapses in hippocampus is one of the major hallmarks of AD. It was determined that whether AG-1061 protected against Aβ1-42-induced synaptotoxicity in the hippocampus. Golgi-Cox staining in the hippocampal slices was performed to visualize and quantify dendritic spines. Aβ1-42 group rats exhibited a significant decrease in the density of dendritic spines in the CA1 region relative to Sham group ($P<0.001$). In contrast, a marked reversal of the dendritic spine loss was observed in Aβ1-42+AG-1061 group ($P<0.01$).

To further investigate the possible molecular mechanisms underlying AG-1061's prevention of Aβ1-42-induced cognitive impairments, levels of SIRT1 and p-CREB hippocampus were determined. Compared with Sham group, the SIRT1 protein level was significantly decreased in the Aβ1-42 group ($P<0.01$), and this decline was prevented by AG-1061 treatment ($P<0.05$). The level of p-CREB was also examined. The Aβ1-42 group showed a decrease in p-CREB level compared to that of Sham group, while AG-1061 treatment significantly increased the expression of p-CREB protein ($P<0.01$, $P<0.05$).

The effect and possible mechanism of AG-1061 on Aβ1-42-induced cognitive impairment in the rat model of AD was determined. It was found that Aβ1-42 injection impaired learning and memory as well as the hippocampal synaptic plasticity in rats, and AG-1061 rescued the impairments by increasing levels of SIRT1 and p-CREB that reduced by Aβ1-42. Cognitive decline in AD patients is associated with elevated brain levels of Aβ1-42. After intracerebroventricular injected Aβ1-42, rodents showed behavioral disabilities including learning and memory impairments in several behavioral tests (Zhang et al., 2015). In the present study, open-field test and novel object recognition test were employed to examine the beneficial effect of AG-1061 on cognitive dysfunction in Aβ1-42 rats. The open field test is preformed because most of the cognitive behavior tests depend on general locomotor activity. In this test, animals showed spontaneous locomotion activity and explorative behaviors when exposed to a new environment. Results demonstrated that AG-1061 improved explorative behavior disabilities by Aβ1-42. In addition, the locomotor activity in this test did not differ between any of the groups. It has been shown that Aβ-exposed rats exhibit hippocampus-dependent learning and memory deficits (Wang et al., 2016). The NOR test is one of the most widely used tests to study the cognitive deficits in AD rat models. These results demonstrated that Aβ1-42 caused the short-term as well as long-term learning and memory deficits in the NOR test performance, while AG-1061 treatment could dramatically reverse these cognitive alterations. Furthermore, the cognitive impairment was not attributed to the differences in locomotion activities of rats. Synaptic plasticity can be considered to be the mechanism that supports learning and memory functions. Considerable evidence indicated that synaptic plasticity deficits were commonly found in brains of AD patients as well as AD model animals (Hémar and Mulle, 2011; Ji and Strittmatter, 2013). LTP, an experimental form of synaptic plasticity in the hippocampus, is considered as a cellular mechanism of learning and memory. DEP induced following LTP, is a phenomenon that reverses the strength of potentiated synapses in LTP process, and is involved in the storage of new information of hippocampus (Qi et al., 2013; Wagner and Alger, 2015). This study showed that Aβ1-42 significantly impaired both LTP and DEP in hippocampus and are consistent with previous studies (Hu et al., 2014; Wang et al., 2016). AG-1061 improved the LTP and DEP impairments that was induced by Aβ1-42 in rats.

Many studies have focused on the neurotoxic effects of Aβ on N-methyl D-aspartate receptors (NMDARs) because NMDA receptors-dependent plasticity is likely to underlie synaptic memory mechanisms (Cullen et al., 1997; Kim et al., 2001). NMDARs are stabilized by the synaptic scaffolding protein postsynaptic density protein 95 (PSD-95) at the postsynaptic membrane of excitatory synapses. Using the subcellular fractionation approach to isolate purified excitatory PSDs from rat hippocampus, it was found that levels of NR2A, NR2B and PSD-95 were reduced in total homogenate (H) and TIF fractions by Aβ1-42, which may lead to the distinctly inhibitory effects on synaptic plasticity. Synaptophysin (SYP) located on synaptic vesicle membrane, was related to the release of neurotransmitters (Chi et al., 2003). The decreased SYP in H and TSF of Aβ1-42 rats in this study was consistent with previous study (Ghumatkar et al., 2018). Nevertheless, the reduced levels of pre- and post-synaptic proteins were elevated by AG-1061. In consequence, it was concluded that AG-1061 up-regulated these synaptic proteins to enhance LTP and DEP that contributed to learning and memory. In addition, synaptic loss is a neuropathological hallmark in hippocampus of AD, which could underlie the learning and memory deficits (Scheff et al., 2006). The deposition of Aβ leads to cognitive deficits by disturbing the synaptic signaling pathways and destroying dendritic spines (Pozueta et al., 2013). Evidences also indicate that protecting the morphology and function of synapses could improve the observed cognitive impairment in animal models of AD (Mcclean and Hölscher, 2014; Wei et al., 2015). In this study, the density of dendritic spine was significantly reduced in Aβ-induced rats; however, this loss was attenuated by AG-1061 treatment, which supported the improvements of synaptic plasticity and cognitive disorders. Additionally, the enhancive levels of SYP and PSD-95, markers of the pre- and post-synapse respectively, also indicated that AG-1061 prevented Aβ1-42-induced synaptic loss. It was further assessed the expressions of SIRT1 and CREB that regulated cognitive functions. It was found that Aβ1-42 reduced SIRT1 expression level in hippocampus, while AG-1061 treatment reversed this suppressive effect. SIRT1 has the positive effect on modulation of learning and memory functions in AD. Julien et al. provided the first direct evidence that decreased SIRT1 transcripts observed in hippocampal CA1 and CA3 regions in brains of AD patients (Julien et al., 2009). In addition, a similar result was observed in a study by R Wang et al., which showed that Aβ1-42 suppressed the hippocampal SIRT1 expression level in brains and led to the synaptic plasticity and spatial learning memory impairments of rats (Wang et al., 2016). Moreover, the enhancement effects of learning and memory formations and LTP induction resulted from resveratrol were blocked in SIRT1 mutant mice (Zhao et al., 2013). Taken together, these studies indicated a positive relationship between SIRT1 and learning and memory functions. Results showed that AG-1061 prevents the reduction of SIRT1 to ameliorate the synaptic plasticity and cognitive deficits induced by Aβ1-42. Recent researches have demonstrated that SIRT1 regulated the post-translational modifications of CREB, a transcriptional regulator and a mediator of learning and memory, to maintain the synaptic plasticity and cognitive function (Gao et al., 2010; Zhao et al., 2013; Herskovits and Guarente, 2014). It was demonstrated that CREB activation was decreased in the exposure of Aβ in cultured hippocampus neurons (Matsuzaki et al., 2006). So, the expressions of CREB and p-CREB were analyzed in hippocampus of rats in our study. These results showed that Aβ1-42 inhibited the expression of CREB and p-CREB, and AG-1061 treatment rescued the reductions. These results indicated that the downregulation of CREB activation attributed to Aβ1-42 toxicity, which regulates the synaptic plasticity and cognitive deficits of rats. Meanwhile, the recovery of CREB activation prevented the impairments induced by Aβ1-42. Results are also in accordance with the previous research that the decrease of p-CREB accompanied the downregulated expression of SIRT1. In the hippocampus, SIRT1 suppressed the expression of microRNA-134 by cooperating with the transcription factor Yin Yang 1 (YY1), which resulted in overexpression of CREB and brain-derived neurotrophic factor (BDNF), thereby regulating synaptic plasticity and memory formation (Gao et al., 2010). Moreover, the upregulation levels of SIRT1 and p-CREB by resveratrol could improve learning and memory functions in AD rats (Wang et al., 2016). Together, the neuroprotective effects of AG-1061 may be attributed to the elevating expressions of SIRT1 and p-CREB.

These findings indicate that Aβ1-42 impair learning and memory showing in behavior, synaptic plasticity and density of dendritic spine in hippocampal CA1 region in vivo. AG-1061 reverses the deficits by increasing the expression levels of SIRT1 and p-CREB reduced by Aβ1-42, which may clarify the neuroprotective effects of AG-1061 on learning and memory and synaptic plasticity.

Example 17 AG-1601 and Alzheimer's Disease

AG1601 improves Aβ42-induced cognitive impairment. It was determined that AG-1601 significantly reversed cognitive impairments in novel-object recognition (NOR) test in the Aβ42 induced AD rat model (see FIGS. 20A-D). The time chart of the experiment is shown in FIG. 20A. The locomotion activities of the animals were observed during the open field test. Comparing with Sham group, the Aβ42 group exhibited a significant decreased number of entries into the center zone (FIG. 20B, P<0.01). However, the number of entries into the center zone was increased dramatically AG1601-treated group (Aβ42+AG1601, FIG. 20B, P<0.05). But no significant effect was observed in the tests of total distance and traveling speed.

The NOR test is based on the spontaneous tendency of rodents to explore novel objects. In the short-term memory test, the recognition index was obviously higher in Sham group than the 50% chance level. However, Aβ42 group animals failed to differentiate the novel object from the familiar object in the short-term memory test, and the recognition index was decreased significantly than the Sham group (FIG. 20B, P<0.01). Moreover, AG1601-treated group showed a significant increase in recognition index compared to the Aβ42 group (FIG. 20C, P<0.05). Similar effect was observed in the long-term memory test (FIG. 20D, P<0.05).

Figure 21A:
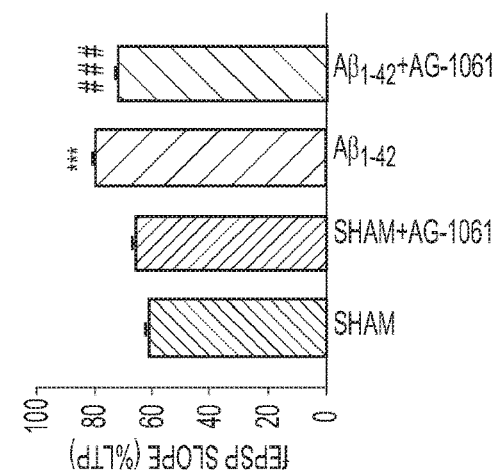
FIG. 21A AG1601 reversed the suppressed LTP and DEP of hippocampus induced by Aβ42. Induced LTP by TBS and DEP by LFS.
Figure 21B:
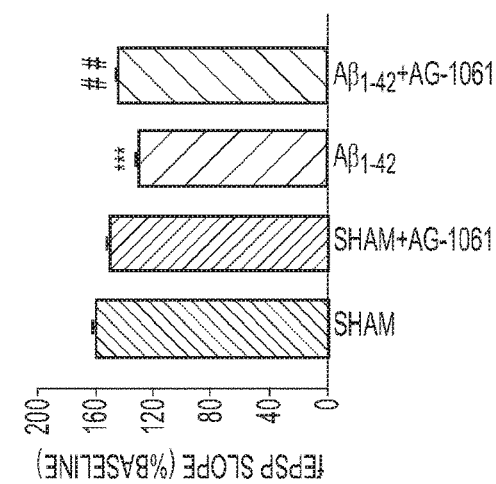
FIG. 21B AG1601 reversed the suppressed LTP and DEP of hippocampus induced by Aβ42. Mean fEPSP slope of LTP.
Figure 21C:
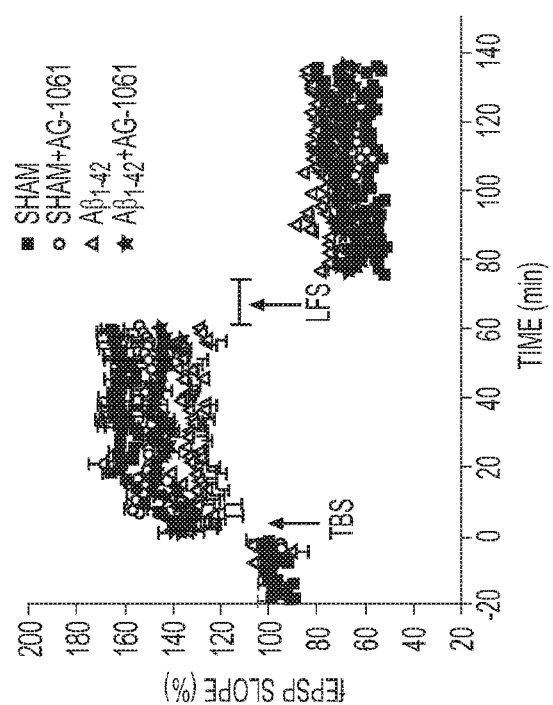
FIG. 21C AG1601 reversed the suppressed LTP and DEP of hippocampus induced by Aβ42. Mean fEPSP slope of DEP.

AG1601 reverses the suppressed LTP and DEP of hippocampus in Aβ42-induced animals. In vivo electrophysiological was used in recording to assess the hippocampal synaptic plasticity in the CA1 region of the animals as shown in FIG. 21A. Based on the last 20 min of recorded data, the field excitatory postsynaptic potential (fEPSP) slopes of LTP (Long-Term Potentiation) were reduced in the Aβ42 group compared with that of sham group (p<0.001). However, the suppressed LTP was significantly recovered by AG-1601 (FIG. 21B, p<0.01, while the increased DEP (depotentiation) caused by Aβ42 were reversed effectively by AG-1061 treatment (FIG. 21C, p<0.001).

Figure 22B:
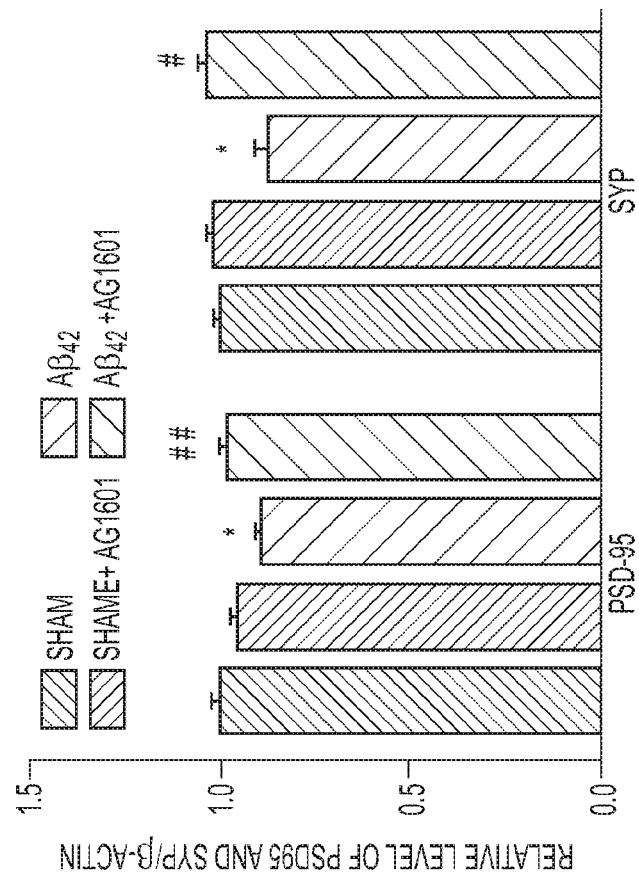
FIG. 22B AG1601 enhanced the expression of reduced synaptic proteins in Aβ42-induced AD model. Quantitative analysis of PSD95 and SYP proteins. * $P<0.05$ vs Shame group, $\#P<0.05$ and $\#\#P<0.01$ vs Aβ42 group; n=3 per group.
Figure 22A:
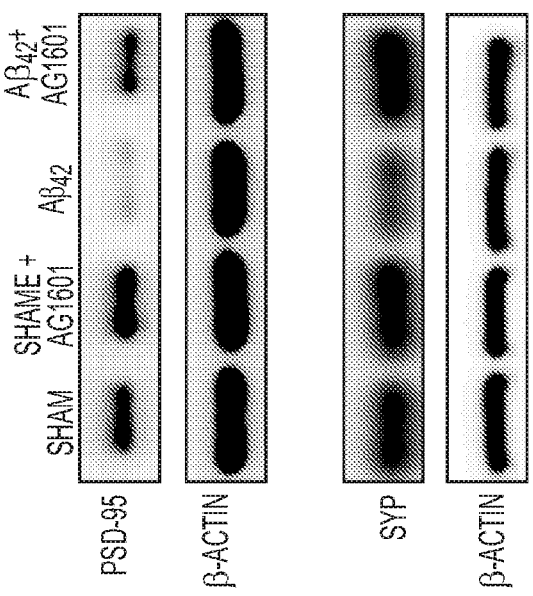
FIG. 22A AG1601 enhanced the expression of reduced synaptic proteins in Aβ42-induced AD model. Homogenates of hippocampal tissues were analyzed by Western blot and detected by individual antibodies as indicated.

AG1601 enhances the expression of synaptic proteins of hippocampus in Ab42-induced animals. To investigate how AG1601 affects Aβ42-induced suppressions of LTP and DEP, the hippocampal synapse tissues were fractionated and assessed for the expression of PSD-95 and SYP by Western blot (FIGS. 22A-B). As shown in FIG. 22A, expressions of both PSD-95 and SYP proteins were dramatically inhibited in the Aβ42-induced animals (P<0.05, FIG. 22B), but this effect was overcome in the AG1601-treated group (P<0.01 for PSD-95 and P<0.01 for SYP, see FIG. 22B). These results indicate that the molecular mechanism of LTP and DEP reversing might be due to the up-regulating the expression levels of synaptic proteins.

AG1601 up-regulates levels of SIRT1 and phosphorylated CREB. SIRT1 is expressed widely in adult brain, and participates in many complex physiological processes including neurogenesis and neuroprotection. It has been reported that SIRT1 is essential for synaptic plasticity and cognitive functions. Overexpression of SIRT1 could protect against AD. CREB (CAMP response element binding protein) is a well-known nucleus transcription factor and CREB phosphorylation (p-CREB) plays a critical role in synaptic plasticity. The long-term potentiation (LTP), a phenomenon of synaptic strengthening, is thought to be the cellular mechanism of learning and memory, the CREB knockout mice showed deficits in both LTP and long-term memory, whereas LTP and memory were enhanced by expressing the active form of CREB. Many studies have been reported that the impaired memory function of AD patients is closely associated with the reduction of CREB activation.

Figure 23A:
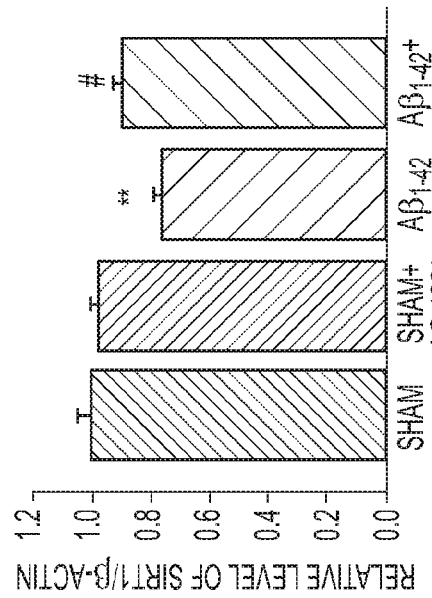
FIG. 23A AG1601 enhanced the expression of reduced SIRT1 proteins in Aβ42-induced AD model. Western blot analysis of the homogenate from hippocampus tissues.
Figure 23B:
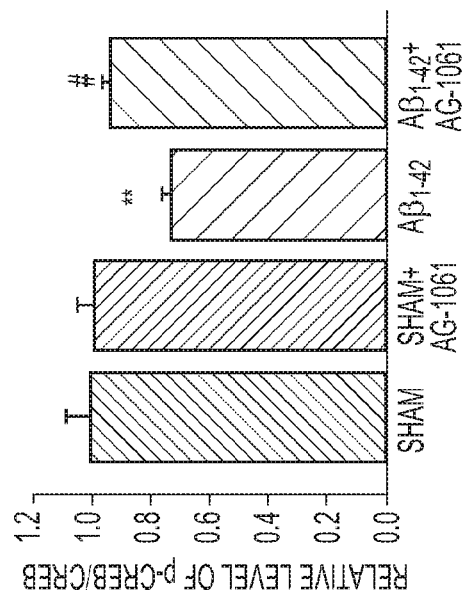
FIG. 23B AG1601 enhanced the expression of reduced SIRT1 proteins in Aβ42-induced AD model. Quantitative analysis of the Western blot result.
Figure 23C:
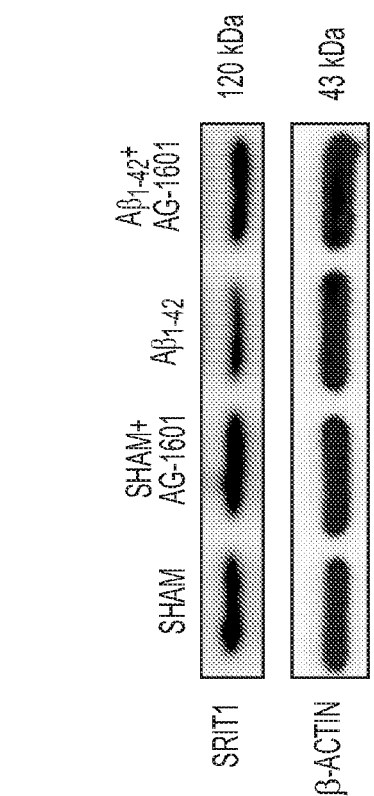
FIG. 23C AG1601 enhanced the expression of reduced p-CREB proteins in Aβ42-induced AD model. Western blot analysis of the homogenate from hippocampus tissues.
Figure 23D:
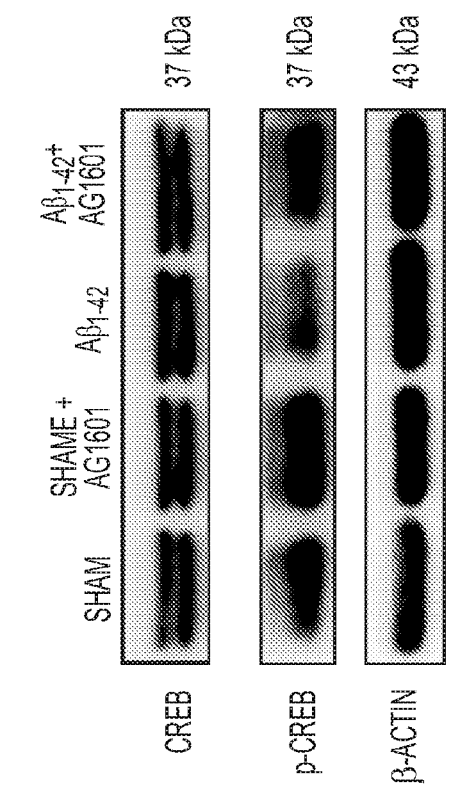
FIG. 23D AG1601 enhanced the expression of reduced p-CREB proteins in Aβ42-induced AD model. Quantitative analysis of the Western blot result.

AG-1601 was also capable of preventing Aβ1-42 induced reduction of SIRT1 and CREB in the density of dendritic spine in CA1 area in AD rat model (FIG. 23A-D). STRT1 was significantly decreased in the Aβ1-42 group, but the decline was prevented by AG-1601 treatment (FIGS. 23A and 4B); p-CREB expression was also significantly increased in AG-1601 treatment compare to the Aβ1-42 (FIGS. 23C and D).

Example 18 Cell Culture and Cell Proliferation Assay

Human glioma cell lines of U251, SF539, SF295 were obtained from NCI/DTP and U87 was obtained from ATCC. U251, SF539, and SF295 cells were grown in RPMI (Gibco) medium; U87 cells were grown in EMEM medium (ATCC), all the cells culture media containing 10% FBS and 100 unit/ml of Penicillin-Streptomycin, and cells were incubated in a 37°C/5% $CO_2$ humidified hood. One day before chemical compounds treatment, four kinds of cells U251, SF539, SF295, and U87 were seeded in 96-well plates at 10,000 cells/well (100 μl) with triplicate. The culture medium was removed and cells were treated with a series different concentration of AG1601/in correspond fresh media. Following an additional incubation of 48 hours at 37° C./5% $CO_2$, cells proliferation assay was performed with Cell Counting Kit-8 (Dojindo Laboratories, #CK04), added 10 μl of reagent to the cells in each well after replacing with 100 μl of fresh media, mix well, following an additional 2 to 3 hours incubation at 37° C./5% $CO_2$, read wavelengths of OD450 nM in a 96-well plate reader (Victor 2, 1420 Multilabel counter), data analysis were performed with Excel and it is platted as relative mean OD450 nM+/−standard error of the mean.

Example 19 GBM Xenograft Mice Model Establish and In Vivo Efficacy Study

Female SHO mice (Crl:SHO-Prkdescid Hr/6-8 weeks) were purchased from Charles River. Human glioblastoma cell line SF295 cells were injected subcutaneously on the right flank of 8 week female SHO mice ($3 \times 10^6$/per mice), tumor appears around one week (day 7) post inoculation. When the tumor size reaches the volume of 100 $mm^3$, total 12 mice were randomly divided to two groups (Treatment & Vehicle). 100 μl of 1.5 μg/μl of AG-1601 (total 150 μg/mice) was injected via IP to each mouse in the Treatment Group every other day for total 28 days; the same volume of $H_2O$ was injected to the mouse in the Vehicle Group. Tumor size measurement was evaluated using the digital calipers and tumor size was calculated using the following formula $[mm^3=((L+W)/4)\times((L+W)/4)\times((L+W)/4)\times 4/3 \times 3.14159]$, data are platted as relative mean tumor volume+/−standard error of the mean.

Example 20

Figures 24A, 24B:
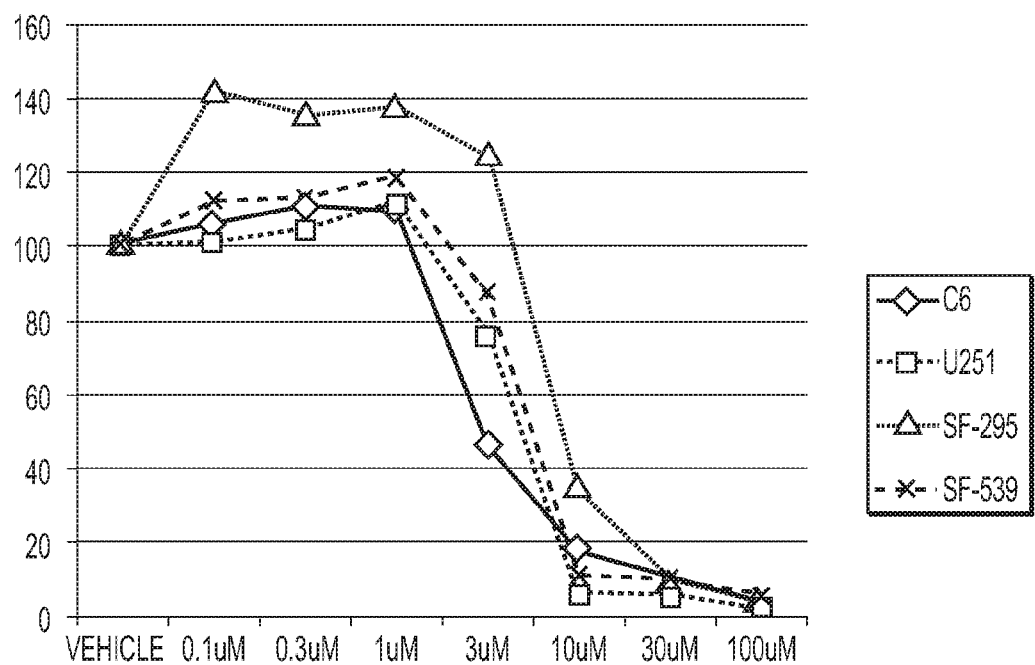
FIG. 24A Efficacy of AG-1601 in rat cells (actual values).
FIG. 24B Efficacy of AG-1601 in rat cell (charted values).
Figures 25A, 25B:
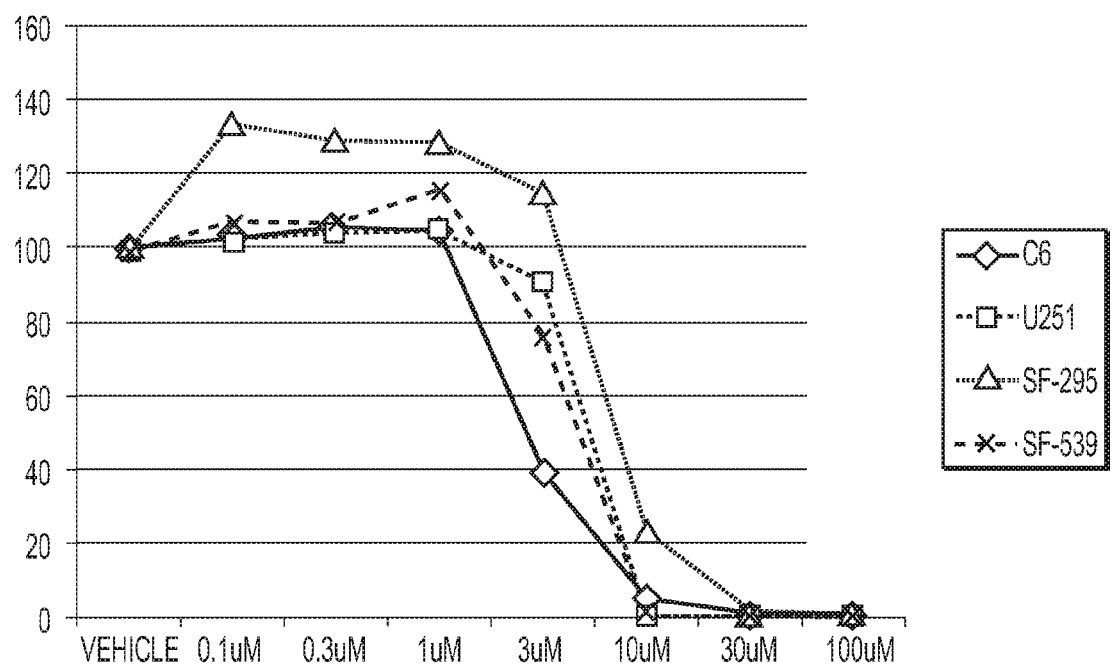
FIG. 25A Efficacy of AG-1601 in human glioma cells (actual values).
FIG. 25B Efficacy of AG-1601 in human glioma cells (charted values).
Figures 26A, 26B:
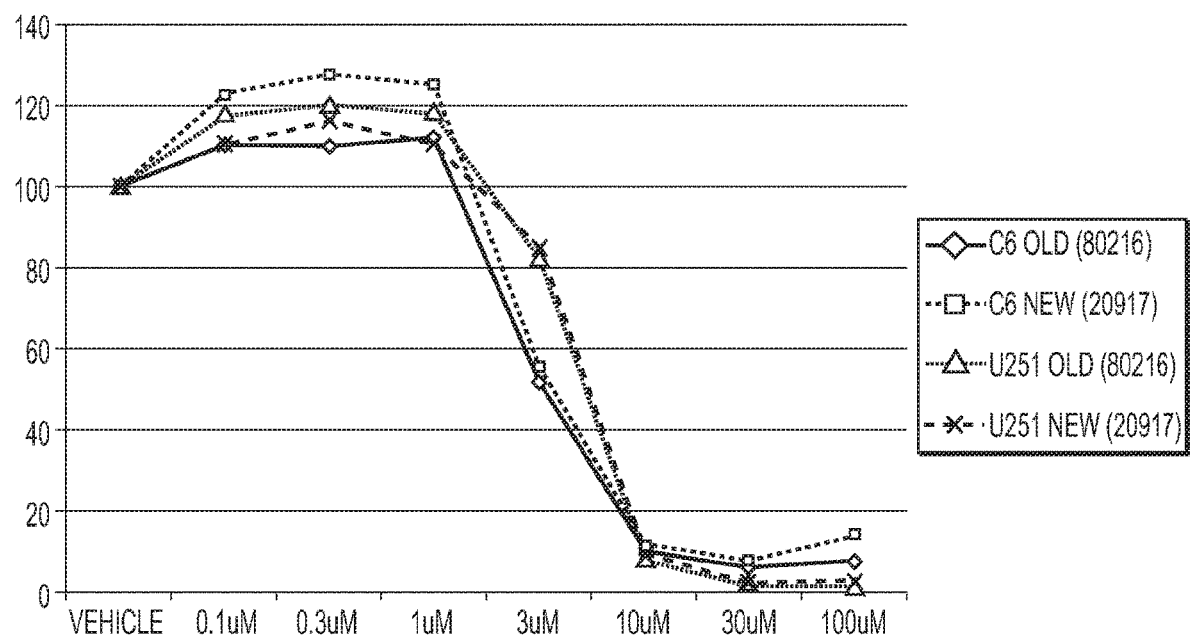
FIG. 26A Efficacy of different batches of AG-1601 in C6 and U251 glioma cells (actual values).
FIG. 26B Efficacy of different batches of AG-1601 in C6 and U251 glioma cells (charted values).
Figures 27A, 27B:
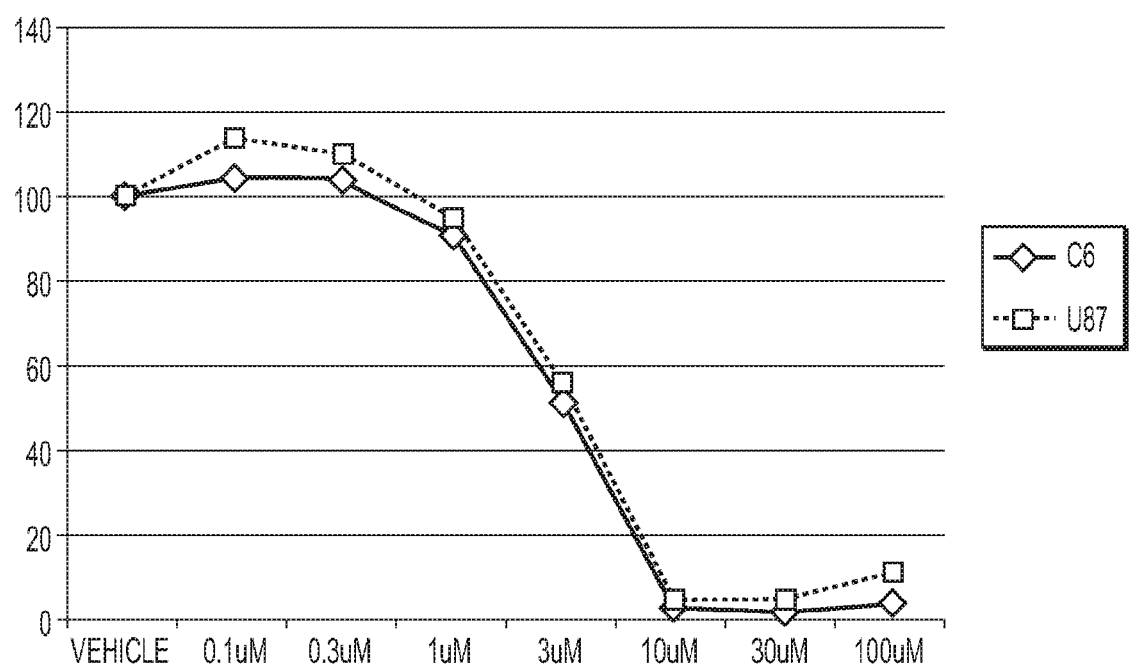
FIG. 27A Efficacy of AG-1601 in C6 and U87 glioma cells (actual values).
FIG. 27B Efficacy of AG-1601 in C6 and U87 glioma cells (charted values).
Figures 28A, 28B:
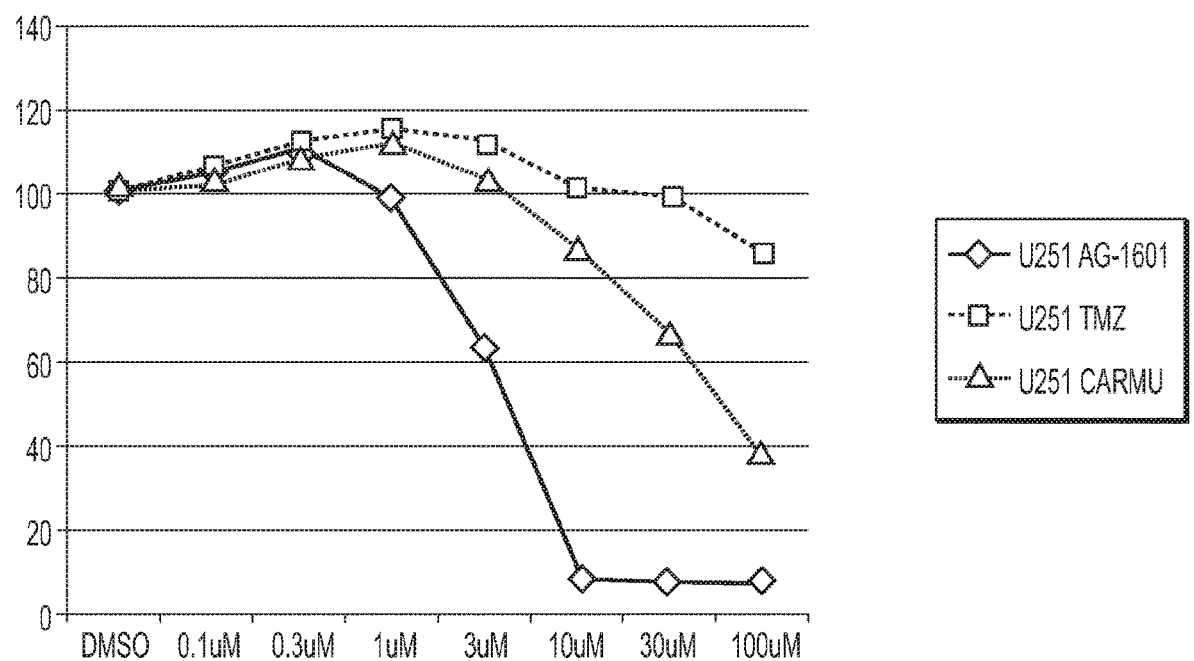
FIG. 28A Efficacy of AG-1601, TMZ, and Carmustine in U251 cells (actual values).
FIG. 28B Efficacy of AG-1601, TMZ, and Carmustine in U251 cells (charted values).
Figures 29A, 29B:
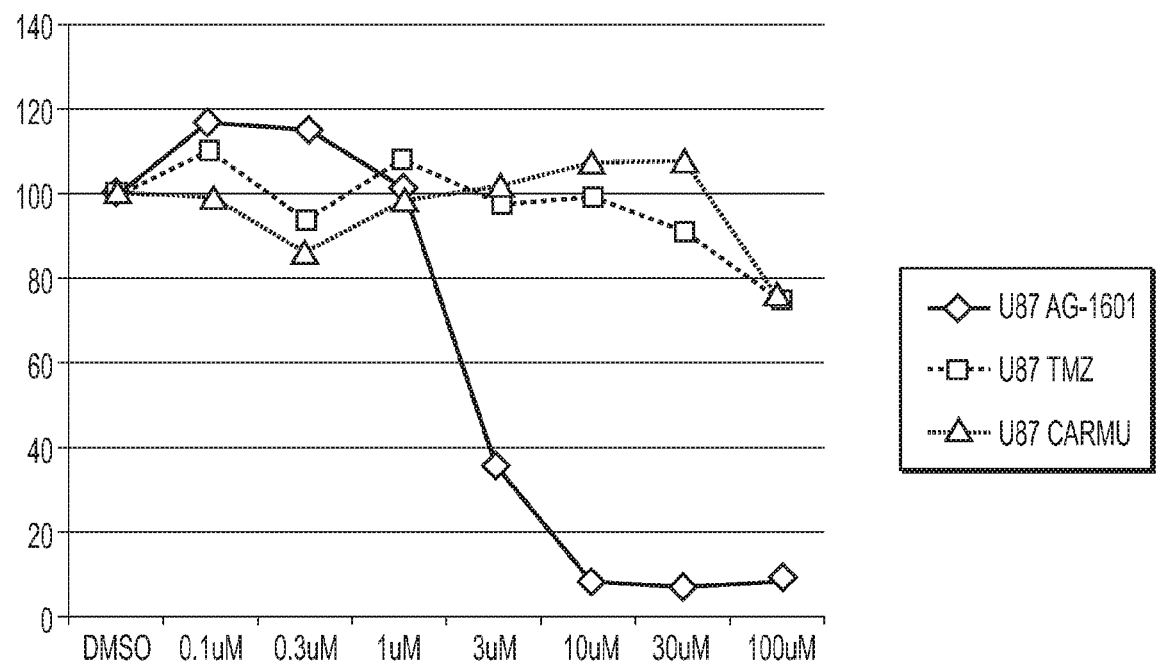
FIG. 29A Efficacy of AG-1601, TMZ, and Carmustine in U87 cells (actual values).
FIG. 29B Efficacy of AG-1601, TMZ, and Carmustine in U87 cells (charted values).
Figure 30:
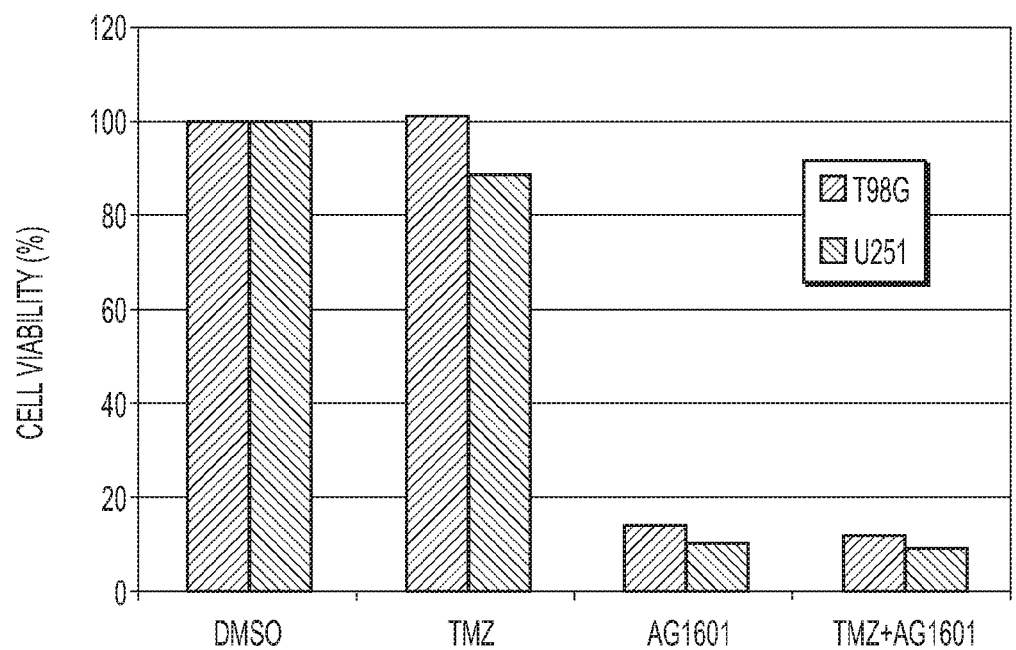
FIG. 30 AG-1601 Overcomes the Effect of TMZ-resistance in T98G cells.

Cells were treated with indicated content of AG-1601 for 48 hours, then followed by performance of cell viability assays. Efficacy of AG-1601 in rat cell (see FIGS. 24A and B), of AG-1601 in human glioma cell see FIGS. 25A and 25B), different batches of AG-1601 in C6 and U251 cells (see FIGS. 26A and 26B), of AG-1601 in C6 and U87 cells (see FIGS. 27A and 27B), of AG-1601, TMZ, and Carmustine in U251 cells (see FIGS. 28A and 28B), and of AG-1601, TMZ, and Carmustine in U87 cells (see FIGS. 29A and 29B). AG1601 showed better efficacy on Glioma cells in vitro than TMZ and Carmustine. Cell viability was determined in T98G cell and U251 cell after treatment with DMSO, TMZ, AG-1601 and TMZ plus AG-1601 (FIG. 30).

Figures 31A, 31B:
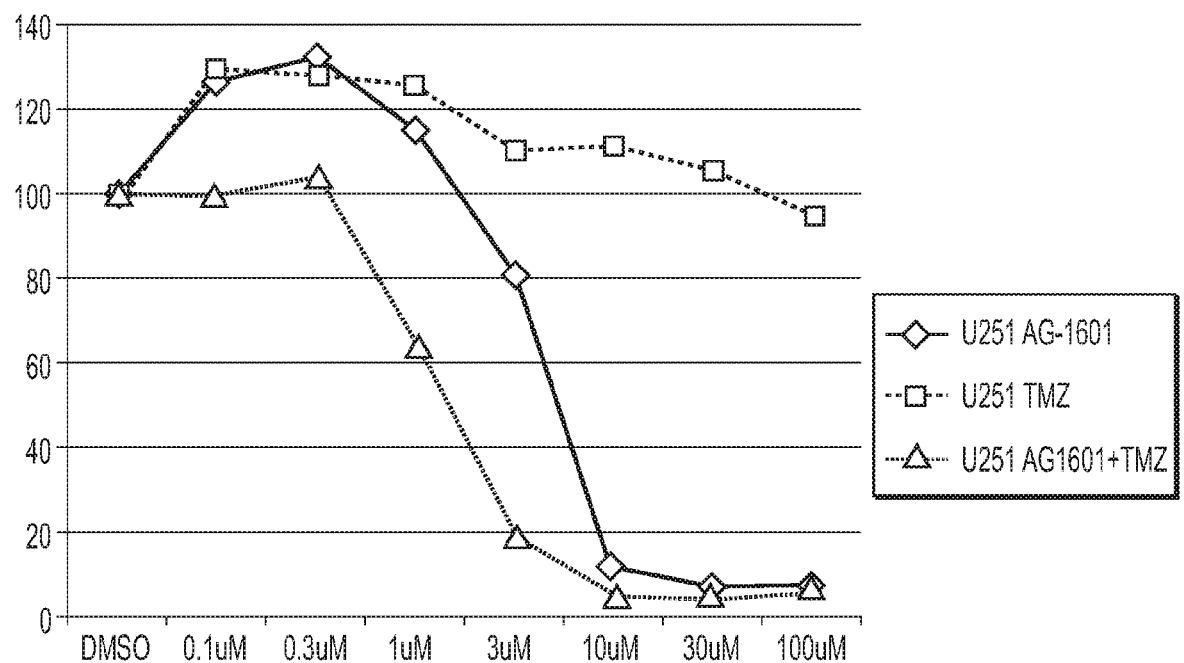
FIG. 31A AG-1601 potentiates the effect of TMZ in U251 cells (actual values).
FIG. 31B AG-1601 potentiates the effect of TMZ in U251 cells (charted values).
Figures 32A, 32B:
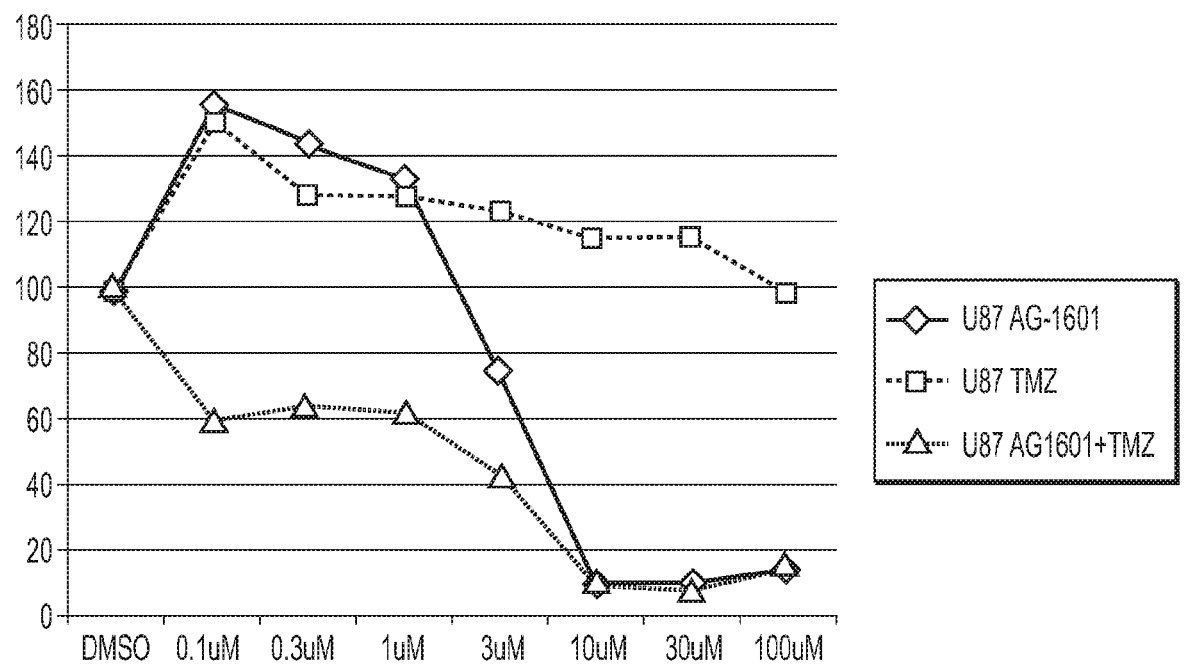
FIG. 32A AG-1601 potentiates the effect of TMZ in U87 cells (actual values).
FIG. 32B AG-1601 potentiates the effect of TMZ in U87 cells (charted values).

As was determined, AG-1601 potentiates the effect of TMZ in U251 cells (see FIGS. 31A and 31B) and in U87 cells (see FIGS. 32A and 32B).

Example 21

AG1601 showed efficacy on SF295 Xenograft tumor mouse model (see FIGS. 33A-D).

Example 22

Figures 34A, 34B:
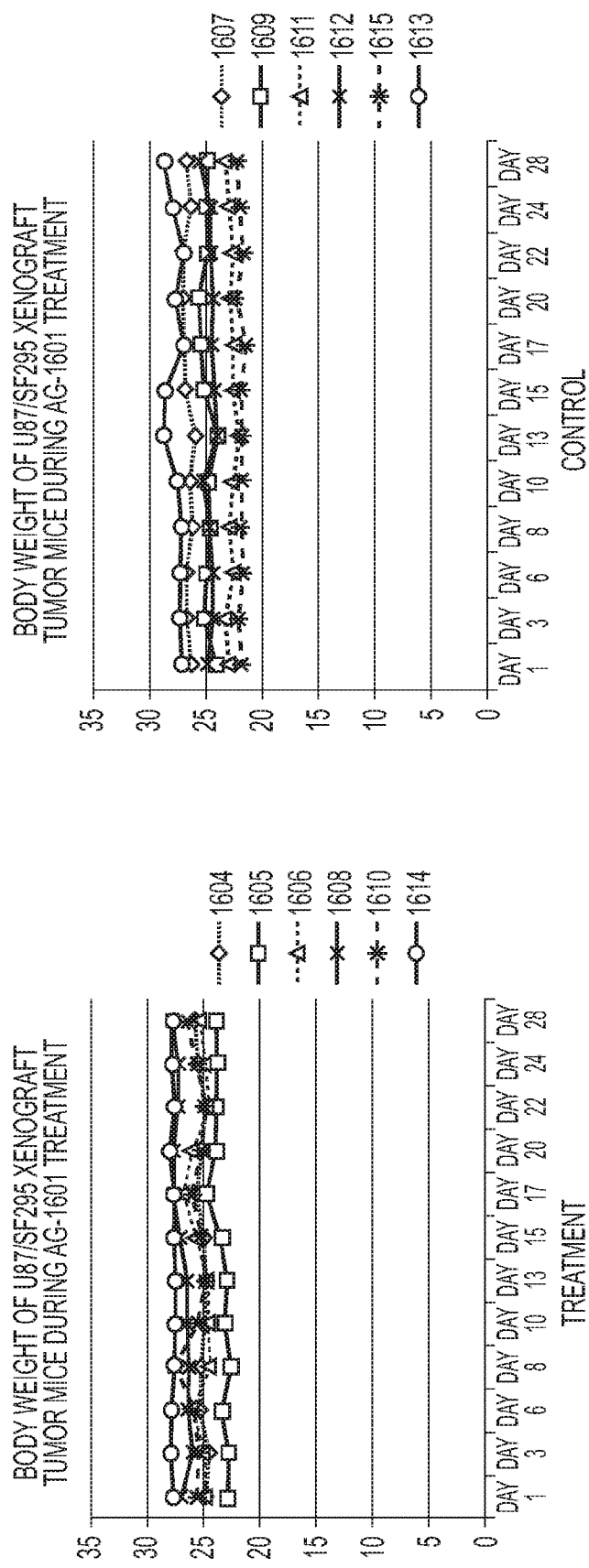
FIG. 34A Body weight of U87/SF295 xenograft tumor mice during AG-1601 treatment (treatment).
FIG. 34B Body weight of U87/SF295 xenograft tumor mice during AG-1601 treatment (control).

AG1601 showed efficacy on C6 Xenograft tumor rat model (see FIG. 34A (treatment) and FIG. 34B (control)).

Example 23

SD male rate were intracranially injected with DMEM medium in 10 μl (sham and small plus AG-1601), and C6 cell at 1×10$^6$ in 10 μl (glioma and glioma plus AG-1601). C6 cells, a type of murine glioma cell lines, were injected into the right striatum in rats to induce glioma formation. C6 cells were cultured in DMEM containing 10% FBS. C6 cells were suspended in DMEM to implant in rats. Rats injected DMEM containing 10% FBS were grouped as Sham. Tumor formation continued for 7 days, followed by AG1601 was intravenous injected once a day for 6 days. Physical findings included: body weight/2d; effects on synaptic plasticity; electrophysiological tests of LTP and CA3-CA1; mechanism of the study (BDNF/TrkB signaling pathway); Western blot; Synaptic plasticity: BDNF/TrkB/PI3K/Akt/NMDA/PSD95/SYP; Tumor suppression: BDNF/TrkB/RAS/ERK/Bcl-2/Bax; Histology and immunohistochemical analysis; HE staining and immunohistochemistry staining; characterization of brain tumor (localization, size, and regions).

Figure 35:
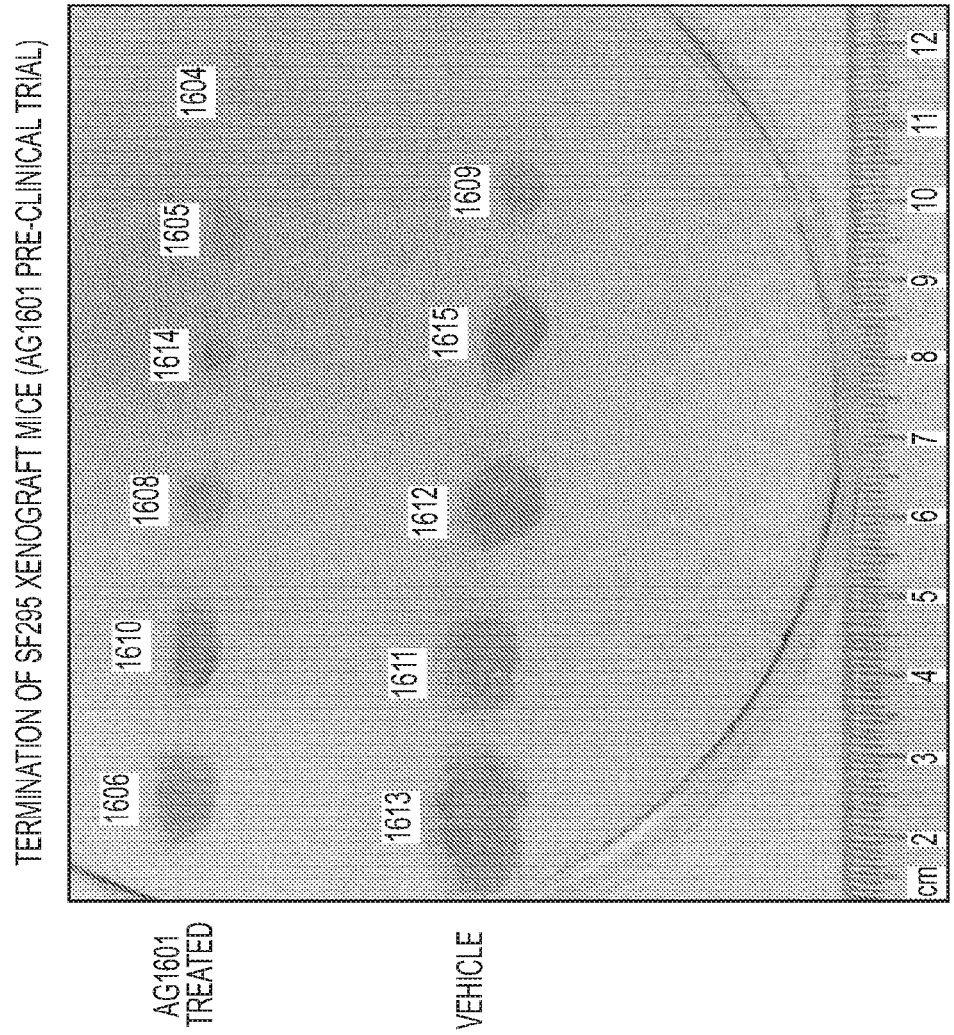
FIG. 35 Tumors isolated from terminated SF295 xenograft mice (AG-1601 pre-clinical trial).
Figure 36:
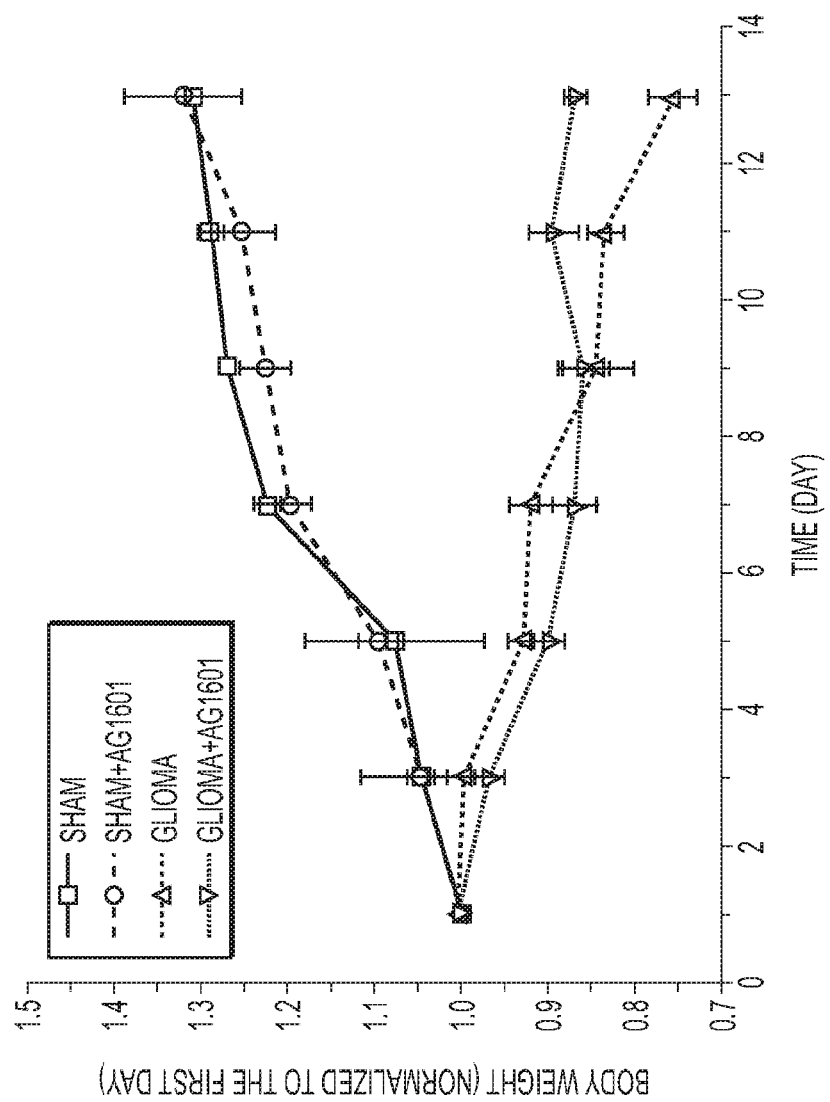
FIG. 36 Body weight of sham, sham plus AG-1601 treated, C6 glioma, and glioma plus AG-1601 treated.
Figure 37:
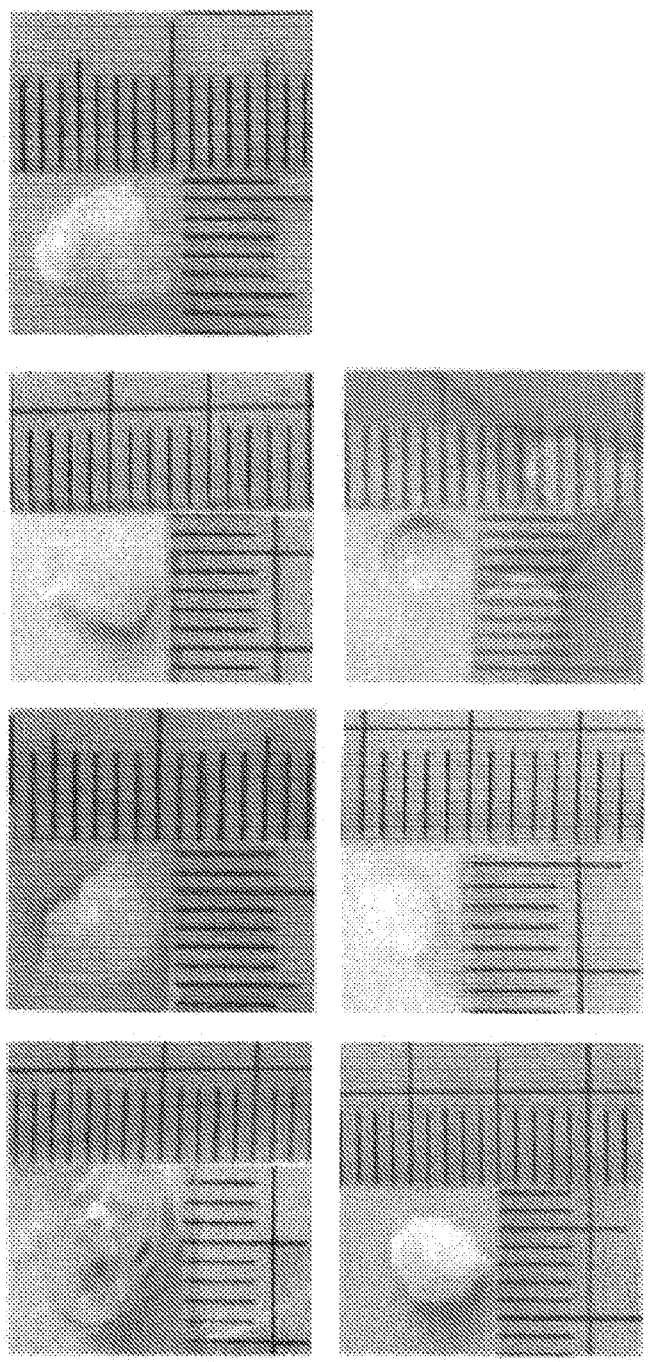
FIG. 37 Images of tumor size of C6 glioma and glioma plus AG-1601.
Figures 38A, 38B:
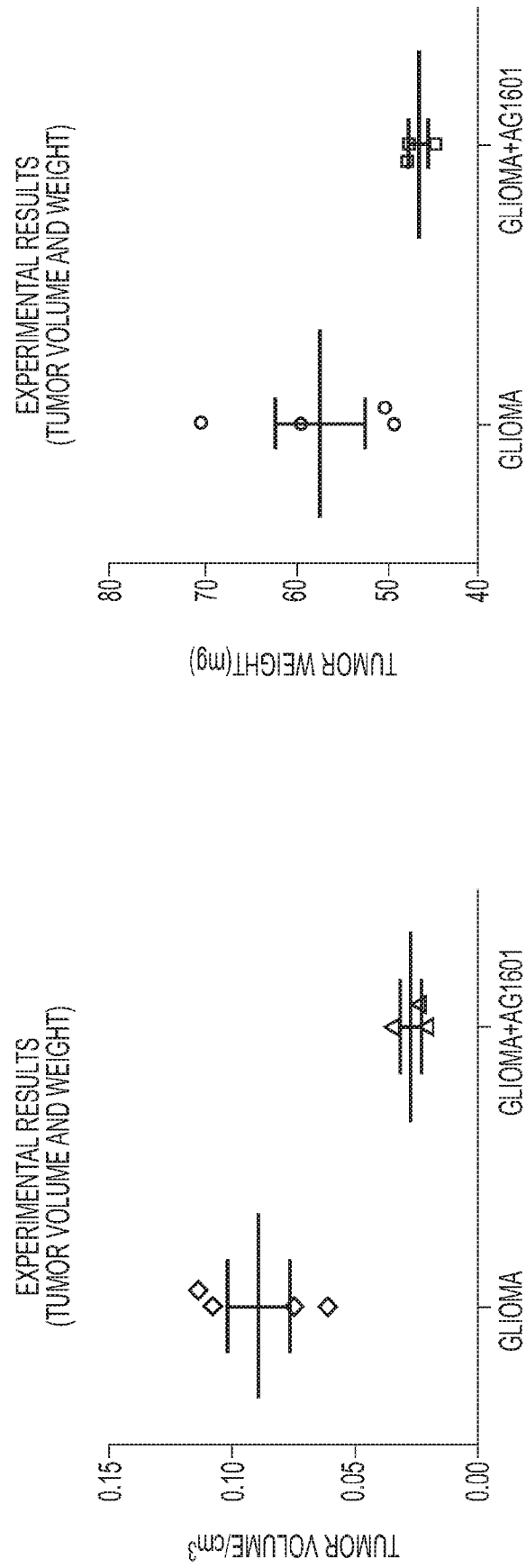
FIG. 38A Tumor volume of C6 glioma and glioma plus AG-1601.
FIG. 38B Tumor weight of C6 glioma and glioma plus AG-1601.
Figure 39:
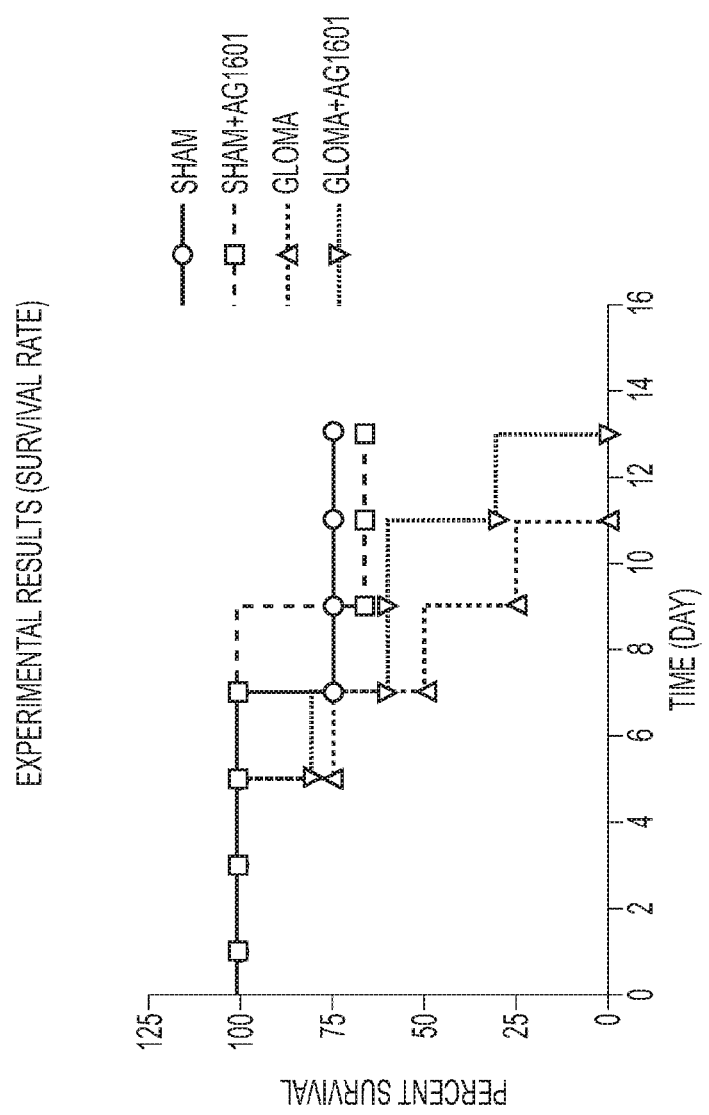
FIG. 39 Survival rates of sham, sham plus AG-1601 treated, C6 glioma, and glioma plus AG-1601 treated.

The body weights in Sham and Sham+AG1601 groups were increased during 2 weeks without significant difference. The body weights in Gloma and Glioma+AG1601 groups were decreased during 2 weeks and significant difference was found between them (see FIGS. 35, 36, 37, 38A, 38B, and 39). Numbers 1604-1615 as shown in FIGS. 33-35 are animal numbers.

Tumors in Glioma and Glioma+AG1601 groups were separated from brains and weighed. Compared to the Glioma group, the volumes and weights correspondingly reduced in Glioma+AG1601 group. These results indicated that AG1601 could suppress glioma growth.

The survival time of rats in the glioma group treated with AG1601 was longer than that in the glioma group without treatment.

The body weights in Sham and Sham+AG1601 groups were increased during 2 weeks without significant difference. The body weights in Gloma and Glioma+AG1601 groups were decreased during 2 weeks and significant difference was found between them. Tumors in Glioma and Glioma+AG1601 groups were separated from brains and weighed. It showed that the volumes and weights correspondingly reduced in Glioma+AG1601 group compared to the Glioma group, suggesting that AG1601 could suppress glioma growth. Survival time of rats treated with AG1601 was longer than that without treatment.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A compound selected from:

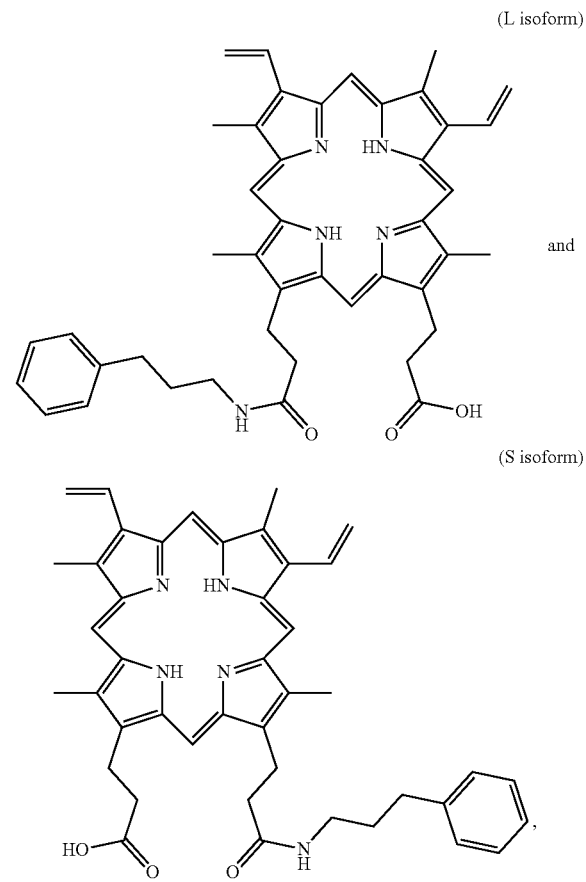

or a combination thereof.

2. The combination of claim 1, wherein the ratio of L isoform to S isoform is approximately 1:1.

3. The combination of claim 1, wherein the ratio of L isoform to S isoform, or the ratio of S isoform to L isoform, is approximately 1:2 or more.

4. A pharmaceutical composition comprising a compound or a combination of claim 1 and a pharmaceutically acceptable carrier.

5. The pharmaceutical composition of claim 4, further comprising an adjuvant.

6. The pharmaceutical composition of claim 5, wherein the adjuvant does not contain aluminum.

7. The pharmaceutical composition of claim 5, wherein the adjuvant contains aluminum.

8. The pharmaceutical composition of claim 4, which is aqueous or freeze-dried.

9. A method of treating glioma in a patient in need thereof, comprising administering to the patient an effective amount of a pharmaceutical composition of claim 4.

10. The method of claim 9, wherein the effective amount is therapeutically or prophylactically effective.

11. A method of treating small cell carcinoma in a patient in need thereof, comprising administering to the patient an effective amount of a pharmaceutical composition of claim 4.

12. A method of treating Alzheimer's disease in a patient in need thereof, comprising administering to the patient an effective amount of a pharmaceutical composition of claim 4.

13. The method of claim 9, wherein the pharmaceutical composition is administered intravenously, intramuscularly or orally.

14. The method of claim 11, wherein the effective amount is therapeutically or prophylactically effective.

15. The method of claim 11, wherein the pharmaceutical composition is administered intravenously, intramuscularly or orally.

16. The method of claim 12, wherein the effective amount is therapeutically or prophylactically effective.

17. The method of claim 12, wherein the pharmaceutical composition is administered intravenously, intramuscularly or orally.

18. The combination of claim 1, wherein the ratio of L isoform to S isoform, or the ratio of S isoform to L isoform, is approximately 1:5 or more.

19. The combination of claim 1, wherein the ratio of L isoform to S isoform, or the ratio of S isoform to L isoform, is approximately 1:10 or more.

20. The combination of claim 1, wherein the ratio of L isoform to S isoform, or the ratio of S isoform to L isoform, is approximately 1:20 or more.

21. The combination of claim 1, wherein the ratio of L isoform to S isoform, or the ratio of S isoform to L isoform, is approximately 1:50 or more.

22. The combination of claim 1, wherein the ratio of L isoform to S isoform, or the ratio of S isoform to L isoform, is approximately 1:100 or more.

* * * * *